(12) United States Patent
Begelman et al.

(10) Patent No.: US 7,860,283 B2
(45) Date of Patent: *Dec. 28, 2010

(54) METHOD AND SYSTEM FOR THE PRESENTATION OF BLOOD VESSEL STRUCTURES AND IDENTIFIED PATHOLOGIES

(75) Inventors: Grigory Begelman, Rishon LeZion (IL); Roman Goldenberg, Haifa (IL); Shai Levanon, Zofit (IL); Shay Ohayon, Haifa (IL); Eugene Walach, Haifa (IL)

(73) Assignee: Rcadia Medical Imaging Ltd., Haifa (IL)

(*) Notice: Subject to any disclaimer, the term of this patent is extended or adjusted under 35 U.S.C. 154(b) by 1035 days.

This patent is subject to a terminal disclaimer.

(21) Appl. No.: 11/562,897

(22) Filed: Nov. 22, 2006

(65) Prior Publication Data

US 2008/0101667 A1    May 1, 2008

Related U.S. Application Data

(60) Provisional application No. 60/862,912, filed on Oct. 25, 2006.

(51) Int. Cl.
*G06K 9/00* (2006.01)

(52) U.S. Cl. ............... 382/128; 382/131; 382/254; 345/418; 345/424; 600/300; 600/407

(58) Field of Classification Search ............... None
See application file for complete search history.

(56) References Cited

U.S. PATENT DOCUMENTS

| | | | |
|---|---|---|---|
| 5,095,521 A | 3/1992 | Trousset et al. | |
| 5,187,658 A | 2/1993 | Cline et al. | |
| 5,235,510 A | 8/1993 | Yamada et al. | |
| 5,343,390 A | 8/1994 | Doi et al. | |
| 5,412,563 A | 5/1995 | Cline et al. | |

(Continued)

FOREIGN PATENT DOCUMENTS

EP    1 225 541 A2    7/2002

(Continued)

OTHER PUBLICATIONS

HeartView CT Application Guide copyright 2004, printed in 2005, Siemens Software (syngo CT 2005A).*

(Continued)

*Primary Examiner*—Sath V Perungavoor
*Assistant Examiner*—Jason Heidemann
(74) *Attorney, Agent, or Firm*—Foley & Lardner LLP

(57) ABSTRACT

A method of presenting information associated with a blood vessel to a user for assessment of the blood vessel is provided. A two-dimensional slice of three-dimensional imaging data of a blood vessel is presented to a user in a first user interface. A blood vessel selection is received from the user. The user selects the blood vessel through an interaction with the first user interface. A blood vessel path associated with the received blood vessel selection is identified from the three-dimensional imaging data. An intensity of the selected blood vessel along the identified blood vessel path is presented to the user for analysis of the selected blood vessel.

3 Claims, 17 Drawing Sheets

U.S. PATENT DOCUMENTS

| | | |
|---|---|---|
| 5,433,199 A | 7/1995 | Cline et al. |
| 5,435,310 A * | 7/1995 | Sheehan et al. ............. 600/416 |
| 5,452,367 A | 9/1995 | Bick et al. |
| 5,457,754 A | 10/1995 | Han et al. |
| 5,458,126 A | 10/1995 | Cline et al. |
| 5,594,638 A | 1/1997 | Iliff |
| 5,647,360 A | 7/1997 | Bani-Hashemi et al. |
| 5,660,176 A | 8/1997 | Iliff |
| 5,671,294 A | 9/1997 | Rogers et al. |
| 5,724,968 A | 3/1998 | Iliff |
| 5,729,620 A | 3/1998 | Wang |
| 5,734,739 A | 3/1998 | Sheehan et al. |
| 5,768,413 A | 6/1998 | Levin et al. |
| 5,769,074 A | 6/1998 | Barnhill et al. |
| 5,779,634 A | 7/1998 | Ema et al. |
| 5,790,690 A | 8/1998 | Doi et al. |
| 5,797,396 A | 8/1998 | Geiser et al. |
| 5,807,256 A | 9/1998 | Taguchi et al. |
| 5,828,774 A | 10/1998 | Wang |
| 5,836,877 A | 11/1998 | Zavisian |
| 5,838,815 A | 11/1998 | Gur et al. |
| 5,854,851 A | 12/1998 | Bamberger et al. |
| 5,868,669 A | 2/1999 | Iliff |
| 5,872,861 A | 2/1999 | Makram-Ebeid |
| 5,881,124 A | 3/1999 | Giger et al. |
| 5,889,524 A * | 3/1999 | Sheehan et al. ............. 345/419 |
| 5,903,664 A | 5/1999 | Hartley et al. |
| 5,970,164 A | 10/1999 | Bamberger et al. |
| 6,011,862 A | 1/2000 | Doi et al. |
| 6,021,404 A | 2/2000 | Moukheibir |
| 6,035,014 A | 3/2000 | Hiraoglu et al. |
| 6,047,080 A | 4/2000 | Chen et al. |
| 6,047,090 A | 4/2000 | Makram-Ebeid |
| 6,067,372 A | 5/2000 | Gur et al. |
| 6,075,879 A | 6/2000 | Roehrig et al. |
| 6,106,466 A | 8/2000 | Sheehan et al. |
| 6,113,540 A | 9/2000 | Iliff |
| 6,138,045 A | 10/2000 | Kupinski et al. |
| 6,148,095 A | 11/2000 | Prause et al. |
| 6,173,077 B1 | 1/2001 | Trew et al. |
| 6,185,320 B1 | 2/2001 | Bick et al. |
| 6,200,268 B1 | 3/2001 | Vince et al. |
| 6,205,350 B1 | 3/2001 | Lorenz et al. |
| 6,206,829 B1 | 3/2001 | Iliff |
| 6,246,784 B1 | 6/2001 | Summers et al. |
| 6,247,004 B1 | 6/2001 | Moukheibir |
| 6,248,063 B1 | 6/2001 | Barnhill et al. |
| 6,249,590 B1 | 6/2001 | Young et al. |
| 6,266,435 B1 | 7/2001 | Wang |
| 6,306,087 B1 | 10/2001 | Barnhill et al. |
| 6,317,509 B1 | 11/2001 | Simanovsky et al. |
| 6,317,617 B1 | 11/2001 | Gilhuijs et al. |
| 6,320,976 B1 | 11/2001 | Murthy et al. |
| 6,345,112 B1 | 2/2002 | Summers et al. |
| 6,351,573 B1 | 2/2002 | Schneider |
| 6,377,832 B1 | 4/2002 | Bergman et al. |
| 6,385,474 B1 | 5/2002 | Rather et al. |
| 6,396,939 B1 | 5/2002 | Hu et al. |
| 6,408,201 B1 | 6/2002 | Foo et al. |
| 6,415,046 B1 | 7/2002 | Kerut, Sr. |
| 6,434,262 B2 | 8/2002 | Wang |
| 6,477,262 B2 | 11/2002 | Wang |
| 6,482,156 B2 | 11/2002 | Iliff |
| 6,501,848 B1 | 12/2002 | Carroll et al. |
| 6,535,821 B2 | 3/2003 | Wang et al. |
| 6,553,356 B1 | 4/2003 | Good et al. |
| 6,556,696 B1 | 4/2003 | Summers et al. |
| 6,574,304 B1 | 6/2003 | Hsieh et al. |
| 6,574,357 B2 | 6/2003 | Wang |
| 6,597,762 B1 | 7/2003 | Ferrant et al. |
| 6,625,303 B1 | 9/2003 | Young et al. |
| 6,628,815 B2 | 9/2003 | Wang |
| 6,643,533 B2 | 11/2003 | Knoplioch et al. |
| 6,662,038 B2 | 12/2003 | Prince |
| 6,674,894 B1 | 1/2004 | Parker et al. |
| 6,684,092 B2 | 1/2004 | Zavislan |
| 6,687,329 B1 | 2/2004 | Hsieh et al. |
| 6,687,405 B1 | 2/2004 | Trew et al. |
| 6,708,055 B2 | 3/2004 | Geiser et al. |
| 6,728,566 B1 | 4/2004 | Subramanyan et al. |
| 6,730,030 B2 | 5/2004 | Palti |
| 6,741,880 B1 | 5/2004 | Foo et al. |
| 6,744,911 B1 | 6/2004 | Avila et al. |
| 6,754,376 B1 | 6/2004 | Turek et al. |
| 6,754,380 B1 | 6/2004 | Suzuki et al. |
| 6,771,262 B2 | 8/2004 | Krishnan |
| 6,771,803 B1 | 8/2004 | Turek et al. |
| 6,782,284 B1 | 8/2004 | Subramanyan et al. |
| 6,785,409 B1 | 8/2004 | Suri |
| 6,795,521 B2 | 9/2004 | Hsu et al. |
| 6,816,743 B2 | 11/2004 | Moreno et al. |
| 6,819,735 B2 | 11/2004 | Bruder et al. |
| 6,819,790 B2 | 11/2004 | Suzuki et al. |
| 6,842,638 B1 | 1/2005 | Suri et al. |
| 6,845,260 B2 | 1/2005 | Liu et al. |
| 6,898,303 B2 | 5/2005 | Armato, III et al. |
| 6,909,797 B2 | 6/2005 | Romsdahl et al. |
| 6,922,462 B2 | 7/2005 | Acharya et al. |
| 6,928,314 B1 | 8/2005 | Johnson et al. |
| 6,937,776 B2 | 8/2005 | Li et al. |
| 6,947,040 B2 | 9/2005 | Tek et al. |
| 6,950,544 B2 | 9/2005 | Ashton |
| 6,978,039 B2 | 12/2005 | Cline et al. |
| 6,983,063 B1 | 1/2006 | Novak et al. |
| 6,985,612 B2 | 1/2006 | Hahn |
| 7,003,144 B2 | 2/2006 | Yim |
| 7,343,187 B2 | 3/2008 | Stetson |
| 2001/0027265 A1 * | 10/2001 | Prince ........................... 600/9 |
| 2001/0043729 A1 | 11/2001 | Giger et al. |
| 2002/0057825 A1 | 5/2002 | Evron et al. |
| 2002/0090121 A1 | 7/2002 | Schneider et al. |
| 2002/0097902 A1 | 7/2002 | Roehrig et al. |
| 2002/0168110 A1 | 11/2002 | Al-Kofahi et al. |
| 2003/0026470 A1 | 2/2003 | Kasai |
| 2003/0028100 A1 | 2/2003 | Tearney et al. |
| 2003/0031351 A1 | 2/2003 | Yim |
| 2003/0053670 A1 | 3/2003 | Hauper et al. |
| 2003/0056799 A1 | 3/2003 | Young et al. |
| 2003/0076987 A1 | 4/2003 | Wilson et al. |
| 2003/0095693 A1 | 5/2003 | Kaufman et al. |
| 2003/0099385 A1 | 5/2003 | Zeng et al. |
| 2003/0122824 A1 | 7/2003 | Chen et al. |
| 2003/0142857 A1 | 7/2003 | Alyassin |
| 2003/0156745 A1 | 8/2003 | Saito et al. |
| 2003/0169914 A1 | 9/2003 | Launay et al. |
| 2003/0174872 A1 | 9/2003 | Chalana et al. |
| 2003/0176780 A1 | 9/2003 | Arnold et al. |
| 2003/0190063 A1 | 10/2003 | Acharya et al. |
| 2003/0215119 A1 | 11/2003 | Uppaluri et al. |
| 2003/0215120 A1 | 11/2003 | Uppaluri et al. |
| 2003/0223627 A1 | 12/2003 | Yoshida et al. |
| 2003/0228040 A1 * | 12/2003 | Oosawa ..................... 382/128 |
| 2004/0022359 A1 | 2/2004 | Acharya et al. |
| 2004/0068167 A1 | 4/2004 | Hsieh et al. |
| 2004/0086175 A1 | 5/2004 | Parker et al. |
| 2004/0096088 A1 | 5/2004 | Kohle |
| 2004/0101179 A1 | 5/2004 | Suryanarayanan et al. |
| 2004/0101181 A1 | 5/2004 | Giger et al. |
| 2004/0101183 A1 | 5/2004 | Mullick et al. |
| 2004/0114800 A1 | 6/2004 | Ponomarev et al. |
| 2004/0120571 A1 | 6/2004 | Duvdevani et al. |
| 2004/0133094 A1 | 7/2004 | Becker et al. |
| 2004/0133100 A1 | 7/2004 | Naghavi et al. |
| 2004/0147838 A1 | 7/2004 | Londt et al. |

| | | | |
|---|---|---|---|
| 2004/0147840 A1 | 7/2004 | Duggirala et al. | |
| 2004/0175034 A1 | 9/2004 | Wiemker et al. | |
| 2004/0190763 A1 | 9/2004 | Giger et al. | |
| 2004/0223636 A1 | 11/2004 | Edic et al. | |
| 2004/0228529 A1 | 11/2004 | Jerebko et al. | |
| 2004/0252870 A1 | 12/2004 | Reeves et al. | |
| 2004/0258285 A1 | 12/2004 | Hansen et al. | |
| 2005/0008210 A1 | 1/2005 | Evron et al. | |
| 2005/0020903 A1 | 1/2005 | Krishnan et al. | |
| 2005/0033139 A1 | 2/2005 | Li et al. | |
| 2005/0033159 A1 | 2/2005 | Mistretta et al. | |
| 2005/0043614 A1 | 2/2005 | Huizenga et al. | |
| 2005/0059876 A1 | 3/2005 | Krishnan et al. | |
| 2005/0069183 A1 | 3/2005 | Ashton | |
| 2005/0074150 A1 | 4/2005 | Bruss | |
| 2005/0093861 A1 | 5/2005 | Moreau-Gobard | |
| 2005/0102315 A1 | 5/2005 | Krishnan | |
| 2005/0105683 A1 | 5/2005 | Sato | |
| 2005/0105786 A1 | 5/2005 | Moreau-Gobard et al. | |
| 2005/0110791 A1 | 5/2005 | Krishnamoorthy et al. | |
| 2005/0111719 A1 | 5/2005 | Pescatore et al. | |
| 2005/0113679 A1 | 5/2005 | Suryanarayanan et al. | |
| 2005/0113960 A1 | 5/2005 | Karau et al. | |
| 2005/0129170 A1 | 6/2005 | Watson et al. | |
| 2005/0136549 A1 | 6/2005 | Gholap et al. | |
| 2005/0143654 A1 | 6/2005 | Zuiderveld et al. | |
| 2005/0147297 A1 | 7/2005 | McLaughlin et al. | |
| 2005/0157848 A1 | 7/2005 | Miyauchi et al. | |
| 2005/0169526 A1 | 8/2005 | Romsdahl et al. | |
| 2005/0185838 A1 | 8/2005 | Bogoni et al. | |
| 2005/0195936 A1 | 9/2005 | Raman et al. | |
| 2005/0201599 A1 | 9/2005 | Matsui | |
| 2005/0201606 A1 | 9/2005 | Okada et al. | |
| 2005/0201618 A1 | 9/2005 | Tek | |
| 2005/0207628 A1 | 9/2005 | Kim | |
| 2005/0207630 A1* | 9/2005 | Chan et al. | 382/131 |
| 2005/0213800 A1 | 9/2005 | Chen et al. | |
| 2005/0232474 A1 | 10/2005 | Wei et al. | |
| 2005/0240094 A1* | 10/2005 | Pichon et al. | 600/407 |
| 2005/0244794 A1 | 11/2005 | Kemp et al. | |
| 2005/0249391 A1 | 11/2005 | Kimmel et al. | |
| 2005/0249392 A1 | 11/2005 | Allain et al. | |
| 2005/0249399 A1 | 11/2005 | Tek et al. | |
| 2005/0251014 A1 | 11/2005 | Qian et al. | |
| 2005/0254546 A1 | 11/2005 | Rittscher et al. | |
| 2005/0256400 A1 | 11/2005 | Raman et al. | |
| 2005/0259854 A1 | 11/2005 | Arimura et al. | |
| 2005/0259855 A1 | 11/2005 | Dehmeshki | |
| 2005/0267337 A1 | 12/2005 | Sakai et al. | |
| 2005/0271271 A1 | 12/2005 | Noble et al. | |
| 2005/0281381 A1 | 12/2005 | Guendel | |
| 2005/0281447 A1 | 12/2005 | Moreau-Gobard et al. | |
| 2005/0286750 A1 | 12/2005 | Dehmeshki | |
| 2006/0004278 A1 | 1/2006 | Giger et al. | |
| 2006/0008143 A1 | 1/2006 | Truyen et al. | |
| 2006/0009694 A1* | 1/2006 | Yousefzadeh et al. | 600/431 |
| 2006/0013460 A1 | 1/2006 | Dehmeshki | |
| 2006/0018524 A1* | 1/2006 | Suzuki et al. | 382/128 |
| 2006/0023924 A1 | 2/2006 | Asbeck et al. | |
| 2006/0153451 A1 | 7/2006 | Hong et al. | |
| 2007/0008317 A1 | 1/2007 | Lundstrom | |
| 2007/0036418 A1* | 2/2007 | Pan et al. | 382/131 |
| 2008/0008366 A1 | 1/2008 | Desh et al. | |
| 2008/0273652 A1 | 11/2008 | Arnold et al. | |
| 2008/0279435 A1 | 11/2008 | Arnold et al. | |

FOREIGN PATENT DOCUMENTS

| | | |
|---|---|---|
| EP | 1 225 542 A2 | 7/2002 |
| EP | 1 387 320 A2 | 2/2004 |
| EP | 1 398 722 A2 | 3/2004 |
| EP | 1 400 910 A2 | 3/2004 |
| EP | 1 426 903 A2 | 6/2004 |
| EP | 1 465 109 A2 | 10/2004 |
| EP | 1 531 423 A2 | 5/2005 |
| EP | 1 531 425 A2 | 5/2005 |
| WO | WO 02/071319 A1 | 9/2002 |
| WO | WO 03/008989 A1 | 1/2003 |
| WO | WO 03/034176 A2 | 4/2003 |
| WO | WO 03/045223 A2 | 6/2003 |
| WO | WO 03/046833 A2 | 6/2003 |
| WO | WO 03/075209 A2 | 9/2003 |
| WO | WO 03/077758 A1 | 9/2003 |
| WO | WO 03/079137 A2 | 9/2003 |
| WO | WO 03/081529 A1 | 10/2003 |

OTHER PUBLICATIONS

White et al. Chest pain evaluation in the emergency department: can MDCT provide a comprehensive evaluation?, AJR, 185(2), 2005, pp. 533-540.*

International Search Report and Written Opinion for PCT/IB2007/003193 dated Oct. 9, 2008.

Kovacs et al., "Automatic Segmentation of the Aortic Dissection Membrane from 3D CTA Images", MIAR 2006, LNCS 4091, pp. 317-324, 2006, Springer-Verlag Berlin Heidelberg 2006.

Masutani et al., "Computerized Detection of Pulmonary Embolism in Spiral CT Angiography Based on Volumetric Image Analysis", IEEE Transactions on Medical Imaging, vol. 21, No. 12, pp. 1517-1523, Dec. 2002.

Non-Final Office Action for U.S. Appl. No. 11/562,771, dated Apr. 26, 2010.

Cardiac CT Application Guide, Version syngo CT 2007A, Siemens Medical, Siemens AG, 2002-2006, printed in 2006, pp. 1-7 & pp. 193-216.

Carrino, J.A., "Digital Image Quality: A Clinical Perspective", in B. Reiner, E. Siegel & J. Carrino (Eds.), Quality assurance: *Meeting the challenge in the digital medical enterprise*, pp. 1-9, 2000, Virginia: SCAR University.

Halon et al., "Resolution of an Intra-Coronary Filling Defect in the Proximal Left Anterior Descending Coronary Artery Demonstrated by 64-Slice Multi-Detector Computed Tomography", *Catheterization and Cardiovascular Interventions*, vol. 67, pp. 246-249, 2006, Wiley-Liss, Inc.

Mansson, L.G., "Methods for the Evaluation of Image Quality: A Review", *Radiation Protection Dosimetry*, vol. 90, Nos. 1-2, pp. 89-99, 2000, Nuclear Technology Publishing.

Notice of Allowance for U.S. Appl. No. 11/562,771, dated Sep. 7, 2010.

Schroeder et al., "Noninvasive detection and evaluation of atherosclerotic coronary plaques with multislice computer tomography", *Journal of the American College of Cardiology*, 2001, vol. 37, No. 5, pp. 1430-1435, Downloaded from www.content.onlinejacc.org on Jul. 1, 2010.

United States Office Action for U.S. Appl. No. 11/562,906, dated Jul. 19, 2010.

United States Office Action for U.S. Appl. No. 11/683,767, dated Jul. 16, 2010.

Chen et al., "Orientation Space Filtering for Multiple Orientation Line Segmentation", May 2000, *IEEE Transactions on Pattern Analysis and Machine Intelligence*, vol. 22, No. 5, pp. 417-429.

Kirbas et al., "A Review of Vessel Extraction Techniques and Algorithms", Jan. 2003, Vision Interfaces and Systems Laboratory (VISLab), Department of Computer Science and Engineering, Wright State University, 52 pp..

United States Non-Final Office Action issued for U.S. Appl. No. 11/562,875, dated Oct. 14, 2010.

Yim et al., "Gray-Scale Skeletonization of Small Vessels in Magnetic Resonance Angiography", Jun. 2000, *IEEE Transactions on Medical Imaging*, vol. 19, No. 6, pp. 568-576.

* cited by examiner

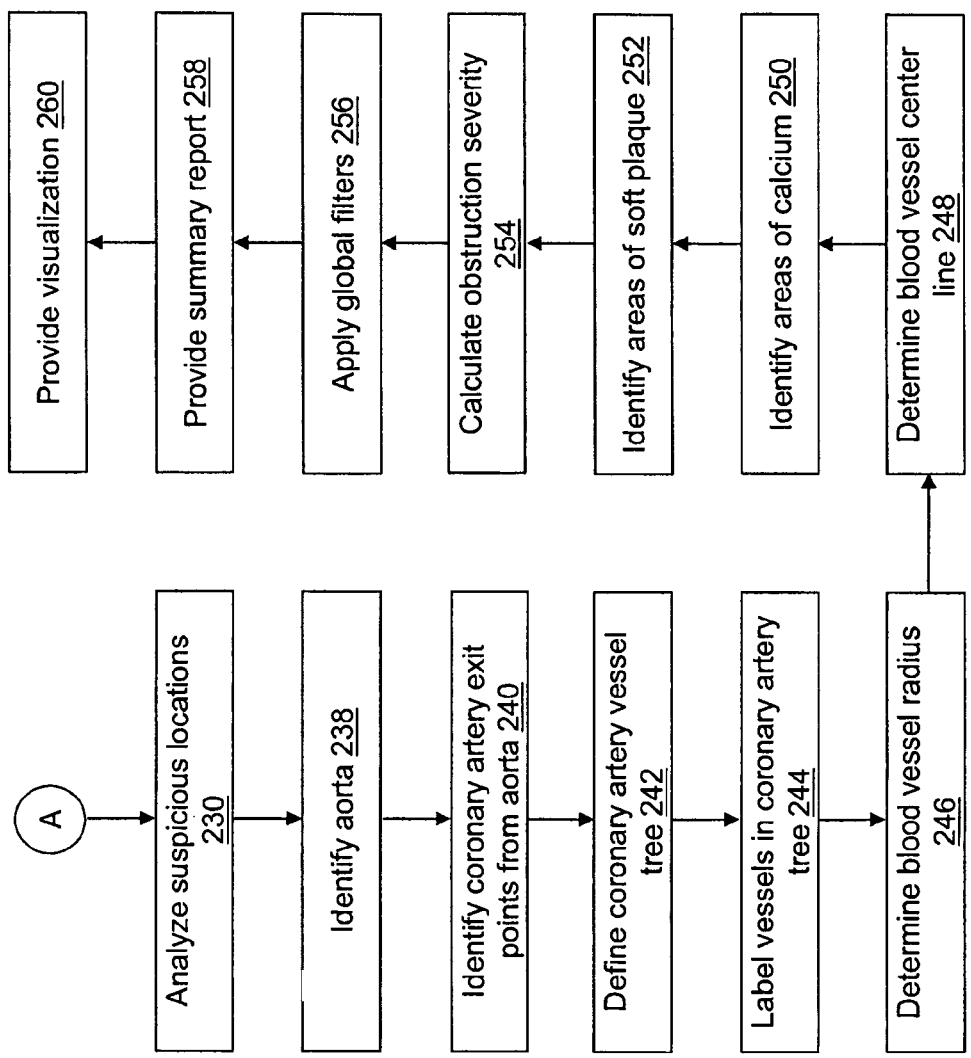

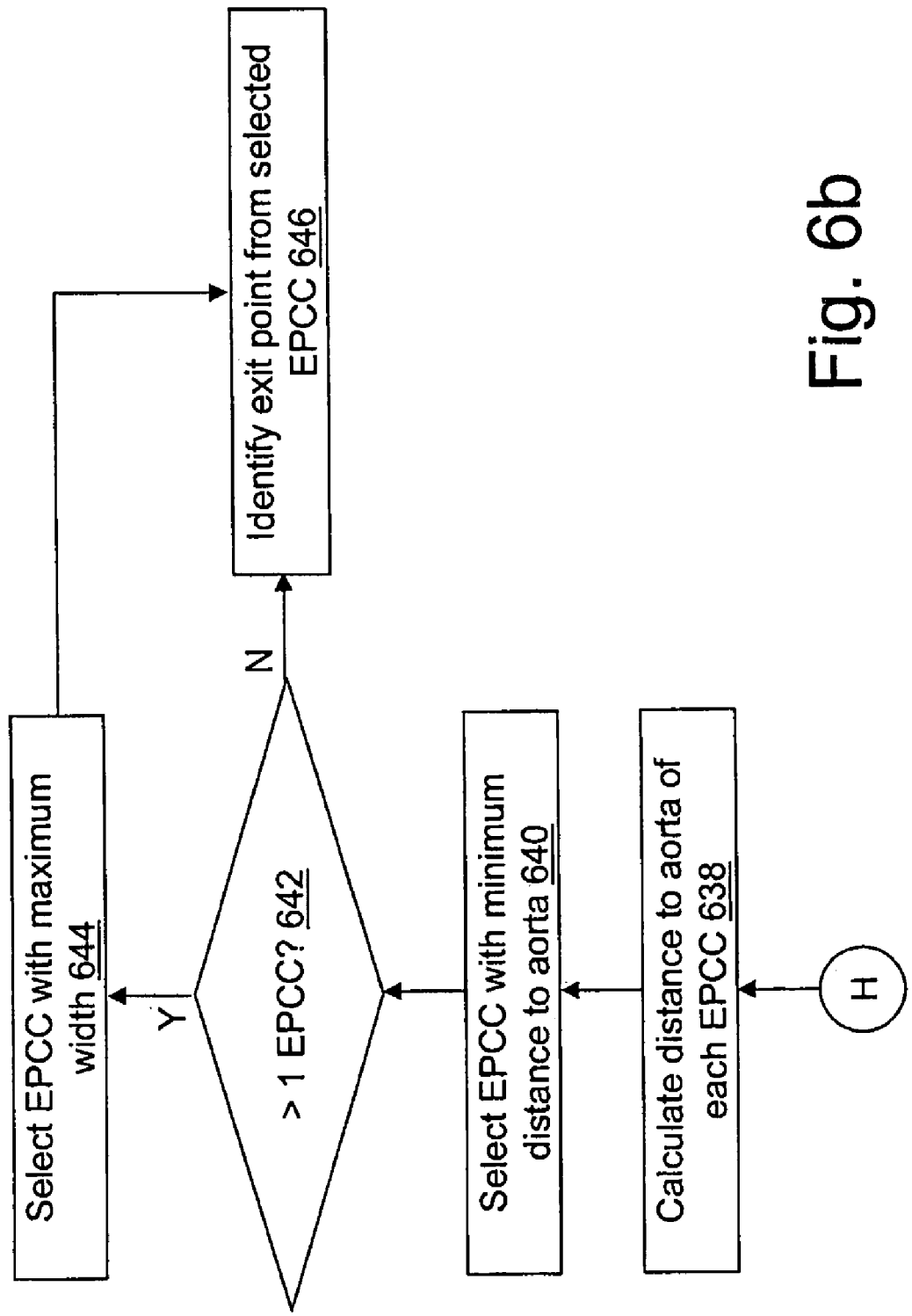

Fig. 11

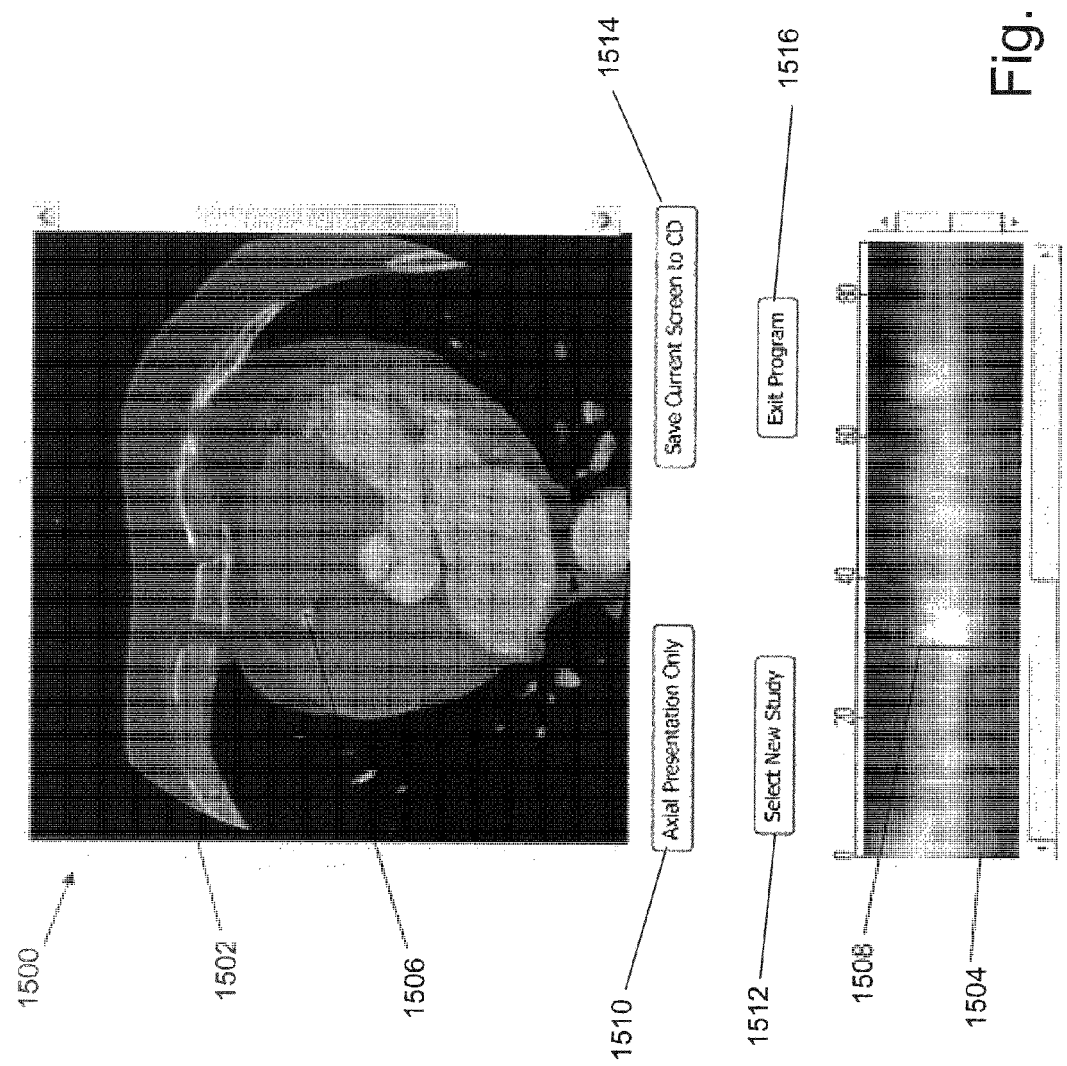

METHOD AND SYSTEM FOR THE PRESENTATION OF BLOOD VESSEL STRUCTURES AND IDENTIFIED PATHOLOGIES

RELATED APPLICATIONS

The present application claims priority to U.S. Provisional Patent Application No. 60/862,912, filed on Oct. 25, 2006, and titled "METHOD AND SYSTEM FOR AUTOMATIC ANALYSIS OF BLOOD VESSEL STRUCTURES AND PATHOLOGIES," the disclosure of which is incorporated herein by reference in its entirety.

FIELD

The field of the disclosure relates generally to computer systems. More specifically, the disclosure relates to automatic analysis of blood vessel structures using a computer system to identify any pathologies in the blood vessels.

BACKGROUND

Chest pain is a common complaint in a hospital or clinic emergency room (ER). Evaluating and diagnosing chest pain remains an enormous challenge. The ER physician generally must quickly rule out three of the most serious and most common possible causes of the chest pain—aortic dissection (aneurysm), pulmonary embolism (PE), and myocardial infarction (coronary artery stenosis). This type of triage is known in the industry as "triple rule out." Until recently, three different classes of diagnostic procedures have been used in the ER to diagnose the three potential possibilities. Today, 64-slice multi-detector, computed tomography systems provide visualization of all three vascular beds—the heart, the lungs, and the thoraco-abdominal aorta. Computed tomography (CT) combines the use of x-rays with computerized analysis of the images. Beams of x-rays are passed from a rotating device through an area of interest in a patient's body from several different angles to create cross-sectional images, which are assembled by computer into a three-dimensional (3-D) picture of the area being studied. 64-slice CT includes 64 rows of detectors, which enable the simultaneous scan of a larger cross sectional area. Thus, 64-slice CT provides an inclusive set of images for evaluating the three primary potential causes of the chest pain.

Existing methods for the analysis of CT image data are semi-automatic and require a radiologist to perform a series of procedures step by step. The radiologist analyzes blood vessels one by one by visually inspecting their lumen and looking for pathologies. This is a tedious, error-prone, and time consuming process. Thus, what is needed is a method and a system for automatically identifying and locating blood vessel pathologies. What is additionally needed is a method and a system for automatically quantifying a level of obstruction of a blood vessel. What is further needed is a method and a system for presenting blood vessel structures and identified pathologies.

SUMMARY

A method and a system for automatic computerized analysis of imaging data is provided in an exemplary embodiment. Coronary tree branches of the coronary artery tree may further be labeled. The analyzed blood vessel may be traversed to determine a location and/or a size of any pathologies. A method and a system for displaying the pulmonary and coronary artery trees and/or aorta and/or pathologies detected by analyzing the image data also may be provided in another exemplary embodiment. The automatic computerized analysis of imaging studies can include any of the features described herein. Additionally, the automatic computerized analysis of imaging data can include any combination of the features described herein.

In an exemplary embodiment, a system for presenting information associated with a blood vessel to a user for assessment of the blood vessel is provided. The system includes, but is not limited to, an imaging apparatus configured to generate imaging data and a processor operably coupled to the imaging apparatus to receive the generated imaging data. The processor is configured to present a two-dimensional slice of three-dimensional imaging data of a blood vessel to a user in a first user interface; to receive a blood vessel selection from the user, wherein the user selects the blood vessel through an interaction with the first user interface; to identify a blood vessel path associated with the received blood vessel selection from the three-dimensional imaging data; and to present an intensity of the selected blood vessel along the identified blood vessel path to the user for analysis of the selected blood vessel.

In an exemplary embodiment, a device for presenting information associated with a blood vessel to a user for assessment of the blood vessel is provided. The device includes, but is not limited to, a memory, the memory capable of storing imaging data defined in three dimensions and a processor operably coupled to the memory to receive the imaging data. The processor is configured to present a two-dimensional slice of three-dimensional imaging data of a blood vessel to a user in a first user interface; to receive a blood vessel selection from the user, wherein the user selects the blood vessel through an interaction with the first user interface; to identify a blood vessel path associated with the received blood vessel selection from the three-dimensional imaging data; and to present an intensity of the selected blood vessel along the identified blood vessel path to the user for analysis of the selected blood vessel.

In another exemplary embodiment, a method of presenting information associated with a blood vessel to a user for assessment of the blood vessel is provided. A two-dimensional slice of three-dimensional imaging data of a blood vessel is presented to a user in a first user interface. A blood vessel selection is received from the user. The user selects the blood vessel through an interaction with the first user interface. A blood vessel path associated with the received blood vessel selection is identified from the three-dimensional imaging data. An intensity of the selected blood vessel along the identified blood vessel path is presented to the user for analysis of the selected blood vessel.

In yet another exemplary embodiment, computer-readable instructions are provided that, upon execution by a processor, cause the processor to implement the operations of the method.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals will denote like elements.

FIGS. 2a and 2b depict a flow diagram illustrating exemplary operations performed by the automated CT image processing system of FIG. 1 in accordance with an exemplary embodiment.

FIGS. 6a and 6b depict a flow diagram illustrating exemplary operations performed in identifying coronary artery vessel exit points from the aorta in accordance with an exemplary embodiment.

FIG. 11 depicts a first user interface of a visualization application presenting summary pathology results in accordance with an exemplary embodiment.

FIG. 15 depicts a fifth user interface of the visualization application presenting multiple views of a pathology in accordance with a third exemplary embodiment.

DETAILED DESCRIPTION

Figure 1:
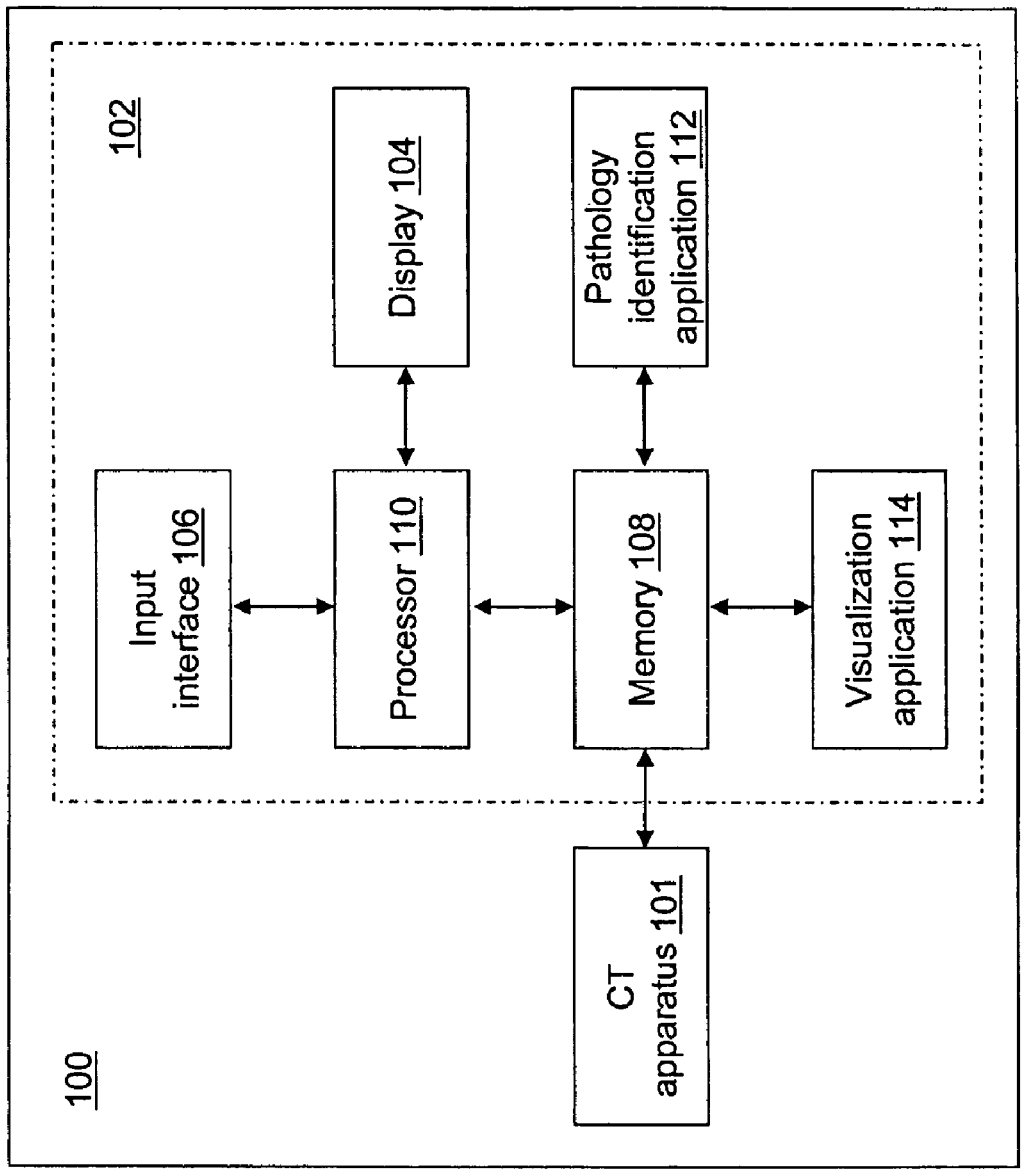
FIG. 1 depicts a block diagram of an automated CT image processing system in accordance with an exemplary embodiment.

With reference to FIG. 1, a block diagram of an image processing system 100 is shown in accordance with an exemplary embodiment. Image processing system 100 may include a CT apparatus 101 and a computing device 102. Computing device 102 may include a display 104, an input interface 106, a memory 108, a processor 110, a pathology identification application 112, and a visualization application 114. In the embodiment illustrated in FIG. 1, CT apparatus 101 generates image data. In general, however, the present techniques are well-suited for use with a wide variety of medical diagnostic system modalities, including magnetic resonance imaging systems, ultrasound systems, positron emission tomography systems, nuclear medicine systems, etc. Moreover, the various modality systems may be of a different type, manufacture, and model. Thus, different and additional components may be incorporated into computing device 102. Components of image processing system 100 may be positioned in a single location, a single facility, and/or may be remote from one another. As a result, computing device 102 may also include a communication interface, which provides an interface for receiving and transmitting data between devices using various protocols, transmission technologies, and media as known to those skilled in the art. The communication interface may support communication using various transmission media that may be wired or wireless.

Display 104 presents information to a user of computing device 102 as known to those skilled in the art. For example, display 104 may be a thin film transistor display, a light emitting diode display, a liquid crystal display, or any of a variety of different displays known to those skilled in the art now or in the future.

Input interface 106 provides an interface for receiving information from the user for entry into computing device 102 as known to those skilled in the art. Input interface 106 may use various input technologies including, but not limited to, a keyboard, a pen and touch screen, a mouse, a track ball, a touch screen, a keypad, one or more buttons, etc. to allow the user to enter information into computing device 102 or to make selections presented in a user interface displayed on display 104. Input interface 106 may provide both an input and an output interface. For example, a touch screen both allows user input and presents output to the user.

Memory 108 is an electronic holding place or storage for information so that the information can be accessed by processor 110 as known to those skilled in the art. Computing device 102 may have one or more memories that use the same or a different memory technology. Memory technologies include, but are not limited to, any type of RAM, any type of ROM, any type of flash memory, etc. Computing device 102 also may have one or more drives that support the loading of a memory media such as a compact disk or digital video disk.

Processor 110 executes instructions as known to those skilled in the art. The instructions may be carried out by a special purpose computer, logic circuits, or hardware circuits. Thus, processor 110 may be implemented in hardware, firmware, software, or any combination of these methods. The term "execution" is the process of running an application or the carrying out of the operation called for by an instruction. The instructions may be written using one or more programming language, scripting language, assembly language, etc. Processor 110 executes an instruction, meaning that it performs the operations called for by that instruction. Processor 110 operably couples with display 104, with input interface 106, with memory 108, and with the communication interface to receive, to send, and to process information. Processor 110 may retrieve a set of instructions from a permanent memory device and copy the instructions in an executable form to a temporary memory device that is generally some form of RAM. Computing device 102 may include a plurality of processors that use the same or a different processing technology.

Pathology identification application 112 performs operations associated with analysis of blood vessel structures and with identification of pathologies associated with the analyzed blood vessels. Some or all of the operations and interfaces subsequently described may be embodied in pathology identification application 112. The operations may be implemented using hardware, firmware, software, or any combination of these methods. With reference to the exemplary embodiment of FIG. 1, pathology identification application 112 is implemented in software stored in memory 108 and accessible by processor 110 for execution of the instructions that embody the operations of pathology identification application 112. Pathology identification application 112 may be written using one or more programming languages, assembly languages, scripting languages, etc. Pathology identification application 112 may integrate with or otherwise interact with visualization application 114.

Visualization application 114 performs operations associated with presentation of the blood vessel analysis and identification results to a user. Some or all of the operations and interfaces subsequently described may be embodied in visualization application 114. The operations may be implemented using hardware, firmware, software, or any combination of these methods. With reference to the exemplary embodiment of FIG. 1, visualization application 114 is implemented in software stored in memory 108 and accessible by processor 110 for execution of the instructions that embody the operations of visualization application 114. Visualization application 114 may be written using one or more programming languages, assembly languages, scripting languages, etc.

CT apparatus 101 and computing device 102 may be integrated into a single system such as a CT imaging machine. CT apparatus 101 and computing device 102 may be connected directly. For example, CT apparatus 101 may connect to computing device 102 using a cable for transmitting information between CT apparatus 101 and computing device 102. CT apparatus 101 may connect to computing device 102 using a network. In an exemplary embodiment, computing device 102 is connected to a hospital computer network and a picture archive, and communication system (PACS) receives a CT study acquired on CT apparatus 101 in an ER. Using PACS, CT images are stored electronically and accessed using computing device 102. CT apparatus 101 and computing device 102 may not be connected. Instead, the CT study acquired on CT apparatus 101 may be manually provided to computing device 102. For example, the CT study may be stored on electronic media such as a CD or a DVD. After receiving the CT study, computing device 102 may start automatic processing of the set of images that comprise the CT study. In an exemplary embodiment, CT apparatus 101 is a 64-slice multi-detector advanced CT scanner having a reconstructed slice width and inter-slice distance less than or equal to approximately 0.5 millimeters (mm), which produces standard digital imaging and communications in medicine (DICOM) images. Computing device 102 may be a computer of any form factor.

Image processing system 100 may provide an initial classification and decision support system, which allows fast and accurate ruling out of the three major diseases associated with chest pain. Image processing system 100 can be provided as a primary CT study inspection tool assisting an ER physician. Additionally, image processing system 100 can be used either to completely rule out some or all of the three diseases (in case of negative results) or as a trigger to call a radiologist and/or a cardiologist to further analyze the case. Additionally, image processing system 100 may automatically identify and segment blood vessel trees and automatically analyze each blood vessel to detect and map all relevant pathologies, including calcified and soft plaque lesions and degree of stenosis.

Figure 2A:
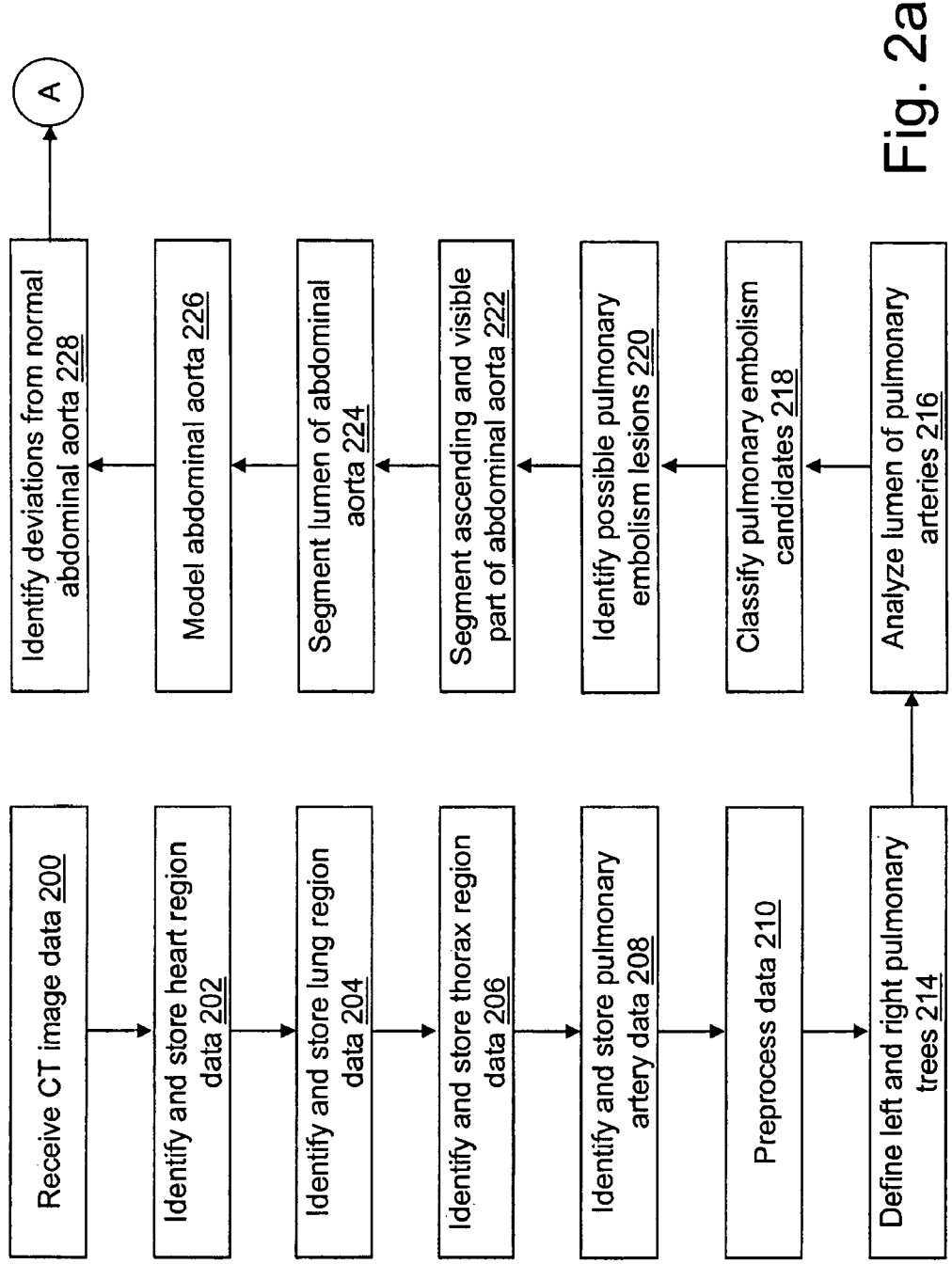

With reference to FIGS. 2a and 2b, exemplary operations associated with pathology identification application 112 and visualization application 114 of FIG. 1 are described. Additional, fewer, or different operations may be performed, depending on the embodiment. The order of presentation of the operations is not intended to be limiting. In an operation 200, pathology identification application 112 receives CT image data. The CT image data may be received from CT apparatus 101 directly or using a network. The CT image data also may be received using a memory medium. In an operation 202, a heart region is identified from the received CT image data. Data associated with the identified heart region is stored at computing device 102. In an exemplary embodiment, the data associated with the identified heart region includes a heart bounding box.

Figure 3:
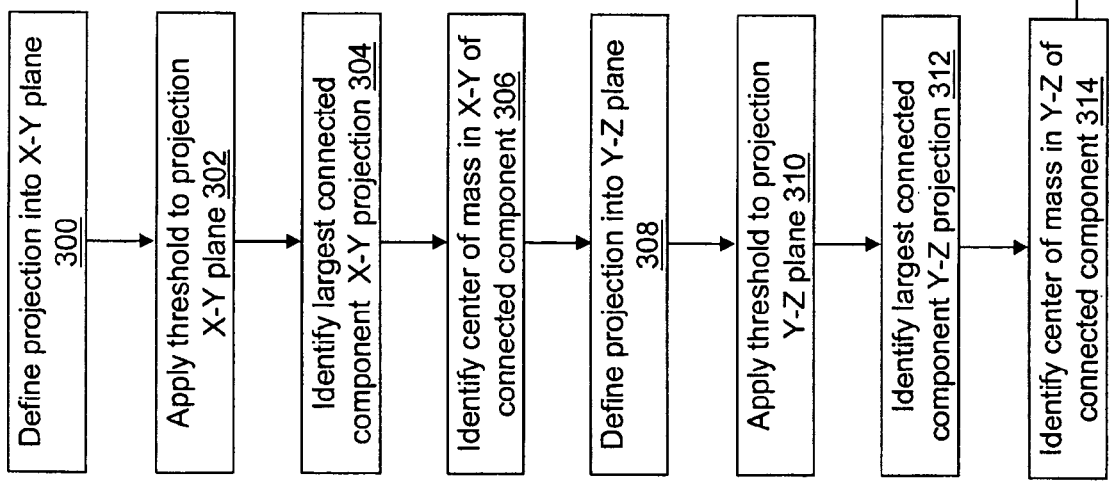
FIG. 3 depicts a flow diagram illustrating exemplary operations performed in detecting a heart region in accordance with an exemplary embodiment.

With reference to FIG. 3, exemplary operations associated with identifying the heart region data are described in accordance with an exemplary embodiment. Additional, fewer, or different operations may be performed, depending on the embodiment. The order of presentation of the operations is not intended to be limiting. For larger studies that may include head and neck or abdominal regions, a determination of the heart region provides a correct anatomical starting point for further segmentation. For smaller studies, a determination of the heart region reduces the size of the processed region and removes the non-relevant areas to reduce the false alarm risk. In an exemplary embodiment, the top and bottom boundaries of the heart region are cut a predetermined distance above and below the heart center.

In an operation 300, a first projection into an X-Y plane is defined. A positive X-axis is defined as extending out from the left side of the body. A positive Y-axis is defined as extending out from the back side of the body. A positive Z-axis is defined as extending out from the head of the body. The first projection is defined by summing the DICOM series along the Z-axis. In an operation 302, a threshold is applied to the first projection. For example, a threshold greater than approximately zero may be applied to eliminate the negative values of air which dominate the region outside the heart region and to retain the positive Hounsfeld unit (HU) values which include the fat, blood, and bones within the heart region. In an operation 304, a first largest connect component (CC) is identified in the thresholded first projection. In an operation 306, a first center of mass of the first largest CC is determined and denoted as $X_c, Y_{c1}$.

In an operation 308, a second projection into a Y-Z plane is defined. The second projection is defined by summing the DICOM series along the X-axis. In an operation 310, a threshold is applied to the second projection data. For example, a threshold greater than approximately zero may be applied to eliminate the negative values of air which dominate the region outside the heart region and to retain the positive HU values which include the fat, blood, and bones within the heart region. In an operation 312, a second largest CC is identified in the thresholded second projection data. In an operation 314, a second center of mass of the second largest CC is determined and denoted as $Y_{c2}, Z_c$. A heart region center is defined as $X_c, Y_{c1}, Z_c$. In an operation 316, a heart region bounding box is defined from the heart region center and an average heart region width in each axis direction, $W_X$, $W_Y$, $W_Z$. In an operation 318, the defined heart region bounding box is stored at computing device 102. The X-axis, Y-axis, Z-axis system centered at $X_c, Y_{c1}, Z_c$ defines a body coordinate system.

Figure 4:
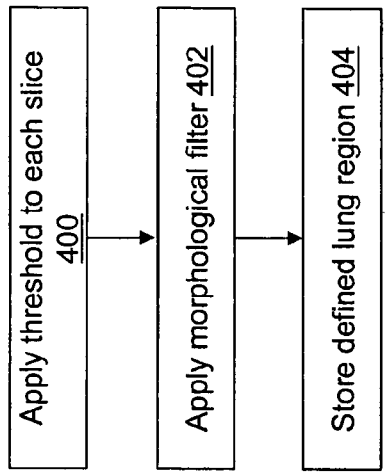
FIG. 4 depicts a flow diagram illustrating exemplary operations performed in detecting a lung region in accordance with an exemplary embodiment.

With reference again to FIG. 2, in an operation 204, a lung region is identified from the received CT image data. Data associated with the identified lung region is stored at computing device 102. In an exemplary embodiment, the data associated with the identified lung region may include a lung mask. With reference to FIG. 4, exemplary operations associated with identifying the lung region data are described in accordance with an exemplary embodiment. Additional, fewer, or different operations may be performed, depending on the embodiment. The order of presentation of the operations is not intended to be limiting. In an operation 400, a lung threshold is applied to each slice of the DICOM series data. For example, a lung threshold of −400 HU may be applied. In an operation 402, a morphological filter is applied to the binary image. In an exemplary embodiment, the binary image is filtered using a morphological closing operation to define a lung region in the CT image data. Other processes for filling holes in the image may be used as known to those skilled in the art. In an operation 404, the defined lung region is stored at computing device 102.

With reference again to FIG. 2, in an operation 206, a thorax region is identified from the received CT image data. Data associated with the identified thorax region is stored at computing device 102. The thorax region may be defined as a convex hull of the lungs and the diaphragm. In an operation 208, the pulmonary arteries are identified from the received CT image data. Data associated with the identified pulmonary arteries is stored at computing device 102.

In an operation 210, the received CT image data is preprocessed. For example, preprocessing may include image enhancement, smoothing, noise reduction, acquisition artifacts detection, etc. Examples of image enhancement algorithms include Gaussian smoothing, median filtering, bilateral filtering, anisotropic diffusion, etc.

In an operation 214, the left and right main pulmonary artery trees are defined. In an operation 216, the lumen of the left and right main pulmonary artery trees is analyzed to identify any pulmonary embolism candidates. In an operation 218, any pulmonary embolism candidates are classified. In an operation 220, possible pulmonary embolism lesions are identified.

In an operation 222, the ascending and the visible part of the abdominal aorta are segmented. In an operation 224, the lumen of the abdominal aorta is segmented. In an operation 226, a 3-D geometry of the abdominal aorta is modeled. In an operation 228, the modeled aorta is compared to a hypothesized "normal" abdominal aorta to identify deviations from the hypothesized "normal" abdominal aorta. In an operation 230, suspicious locations are detected and analyzed to identify dissections and aneurysms.

In an operation 238, the aorta is identified. The aorta is detected in the first imaging slice of the heart region bounding box based, for example, on intensity and shape properties including circularity, compactness, and area. The remainder of the aorta is identified by moving from slice to slice and looking for a similar 2-D object in each slice. Data associated with the identified aorta is stored at computing device 102. In an exemplary embodiment, the data associated with the identified aorta includes an aorta shape and boundary in the identified heart region. It is assumed that the heart region bounding box detected on the previous step includes the aorta exit from the heart and that the cross section of the aorta in the upper slice of the heart region is approximately circular.

Figure 5A:
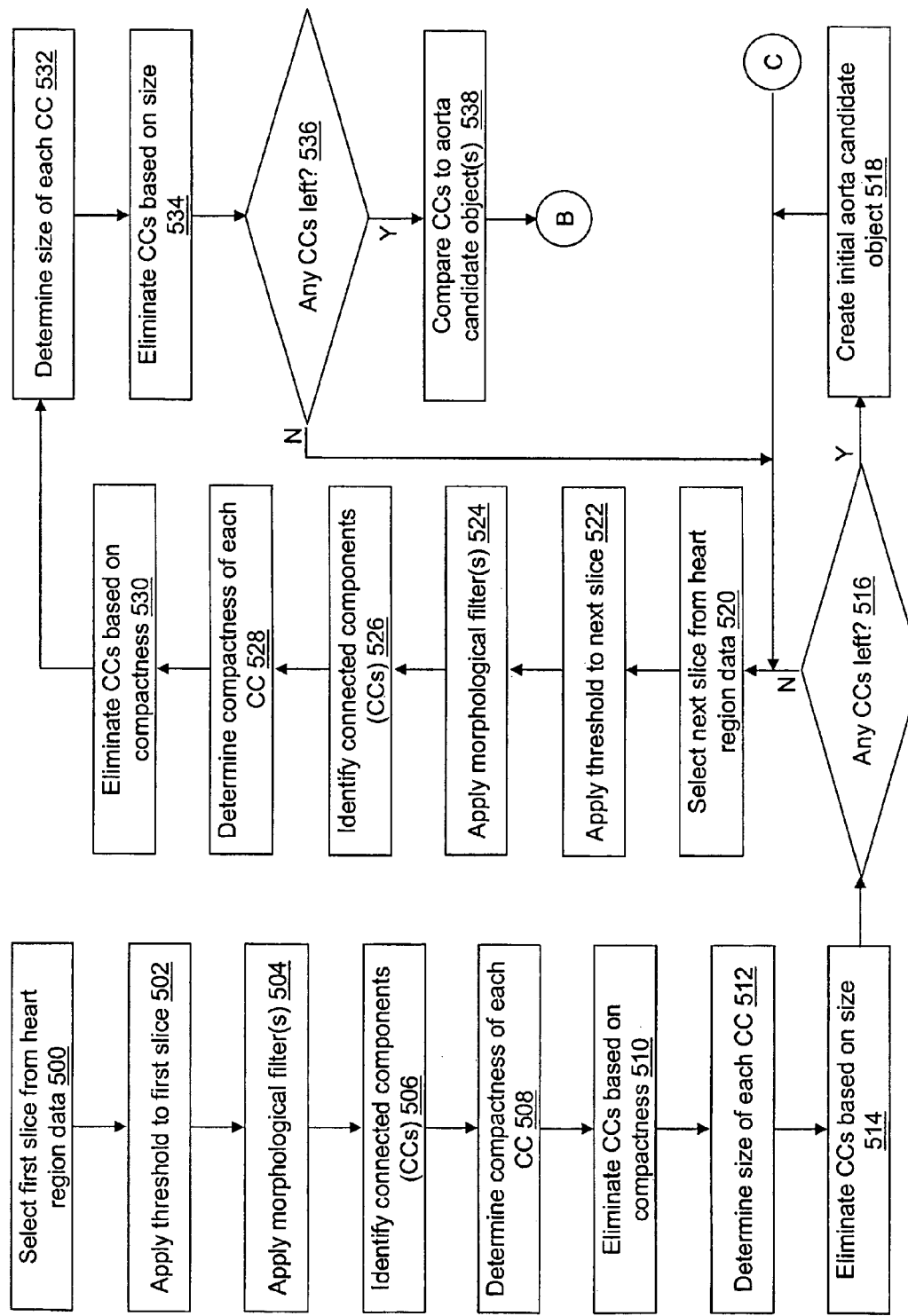
FIGS. 5a and 5b depict a flow diagram illustrating exemplary operations performed in detecting and identifying the aorta in accordance with an exemplary embodiment.
Figure 5B:
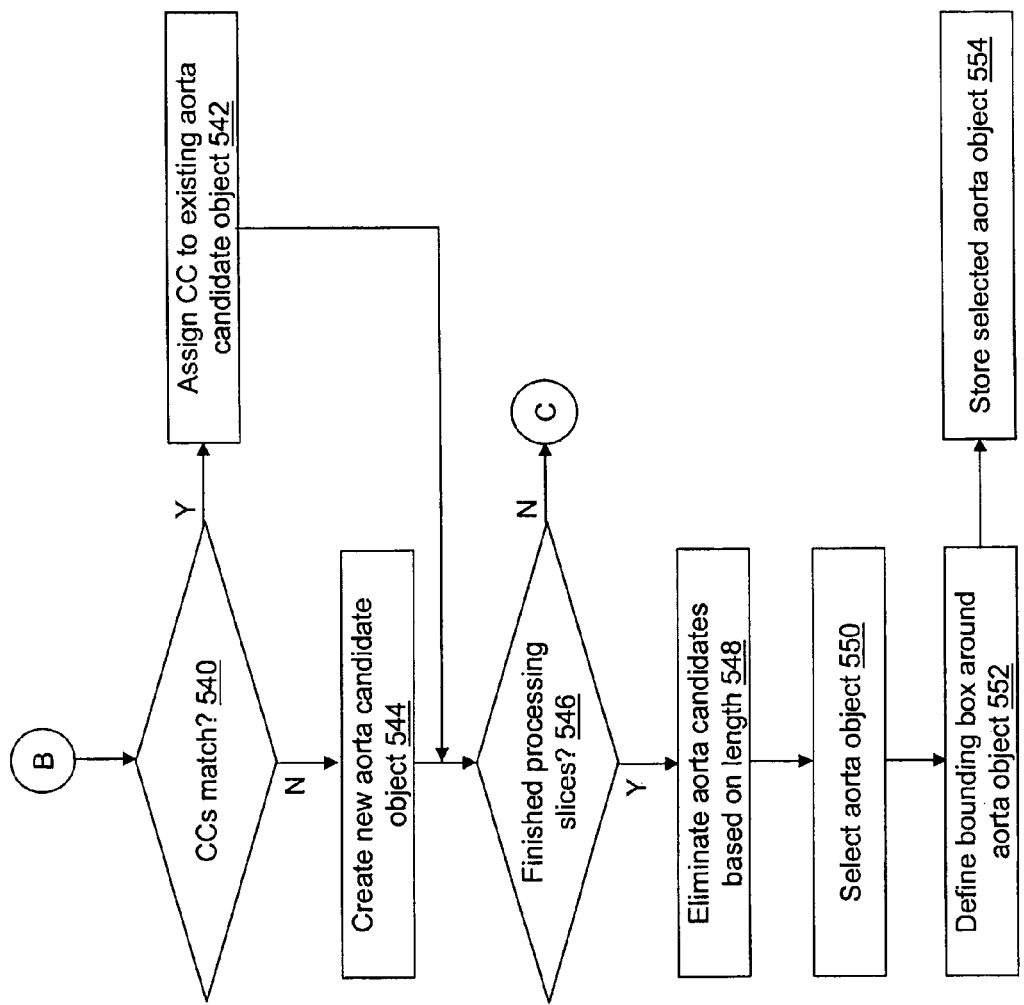

With reference to FIGS. 5a and 5b, exemplary operations associated with identifying the aorta are described in accordance with an exemplary embodiment. Additional, fewer, or different operations may be performed, depending on the embodiment. The order of presentation of the operations is not intended to be limiting. In an operation 500, a first slice is selected from the heart region data. In an operation 502, an aorta threshold is applied to the first slice of the DICOM series data. For example, a lung threshold of 200 HU may be used. In an operation 504, a morphological filter is applied to the binary image. In an exemplary embodiment, the binary image is filtered using a series of morphological filtering operators including an opening operator using a first parameter. In an operation 506, one or more CCs are identified.

In an operation 508, a compactness of each identified CC is determined. In an operation 510, identified CCs having a determined compactness that exceeds a compactness threshold are eliminated from further consideration. A compactness measure of a shape is a ratio of the area of the shape to the area of a circle (the most compact shape) having the same perimeter. The ratio may be expressed mathematically as $M=4\pi(area)/2(perimeter)$. In an exemplary embodiment, the compactness threshold is 0.75. In an operation 512, a size of each identified connected component is determined. In an operation 514, identified CCs having a size that exceeds a maximum size threshold or that is below a minimum size threshold are eliminated from further consideration. In an exemplary embodiment, the maximum size threshold is 10,000 pixels. In an exemplary embodiment, the minimum size threshold is 1,000 pixels. In an operation 516, a determination is made concerning whether or not any identified CCs remain for consideration. If identified CCs remain for consideration, processing continues at an operation 518. If no identified CCs remain for consideration, processing continues at an operation 520. In operation 518, an initial aorta candidate is selected from the remaining CCs. For example, if a plurality of identified CCs remain for consideration, the largest candidate CC that is foremost in the body is selected as the initial aorta candidate.

In operation 520, a next slice is selected from the heart region data. In an operation 522, the aorta threshold is applied to the next slice of the DICOM series data. In an operation 524, the morphological filter is applied to the binary image. In an operation 526, one or more CCs are identified. In an operation 528, a compactness of each identified CC is determined. In an operation 530, the identified CCs having a determined compactness that exceeds the compactness threshold are eliminated from further consideration. In an operation 532, a size of each identified connected component is determined. In an operation 534, the identified CCs having a size that exceeds the maximum size threshold or that is below the minimum size threshold are eliminated from further consideration. In an operation 536, a determination is made concerning whether or not any identified CCs remain for consideration in the current slice. If identified CCs remain for consideration, processing continues at an operation 538. If no identified CCs remain for consideration, processing continues at operation 520.

In operation 538, the identified CCs from the current slice are compared with the aorta candidate object(s) created from the previous slice(s). In an operation 540, a determination is made concerning whether or not any identified CCs match CCs identified from the previous slices. In an operation 542, if a match is found between a CC and an aorta candidate object, the matched CC is assigned to the aorta candidate object. For example, if a center of a CC is closer than twenty pixels to the center of an aorta candidate object, the CC may be identified as matched with the aorta candidate object. In an operation 544, if a match is not found between a CC and an aorta candidate object, a new aorta candidate object is created based on the CC.

In an operation 546, a determination is made concerning whether or not all of the slices have been processed. If slices remain, processing continues at operation 520. If no slices remain, in an operation 548, aorta candidate objects are eliminated based on length. For example, aorta candidate objects that persist for less than 20 slices may be removed from further consideration. In an operation 550, an aorta object is selected from the remaining aorta candidate objects. For example, the aorta candidate object closest to the upper left corner of the image may be selected as the aorta object. In an operation 552, a bounding box is defined around the selected aorta object to identify a region in which the aorta is located in the CT image data. In an operation 554, the selected aorta object is stored at computing device 102.

With reference again to FIG. 2, in an operation 240, exit points of the coronary arteries from the aorta are identified by evaluating all structures connected to the aorta object which look like a vessel. The direction of the vessel near a link point with the aorta object should be roughly perpendicular to an aorta centerline. Additionally, the left and right coronary arteries are expected to exit from the aorta object in a certain direction relative to the body coordinate system. If there are several exit point candidates, the exit point candidate which leads to a larger blood vessel tree is selected. It is assumed that the selected aorta object includes the points where the left and right coronary trees connect with the aorta.

Figure 6A:
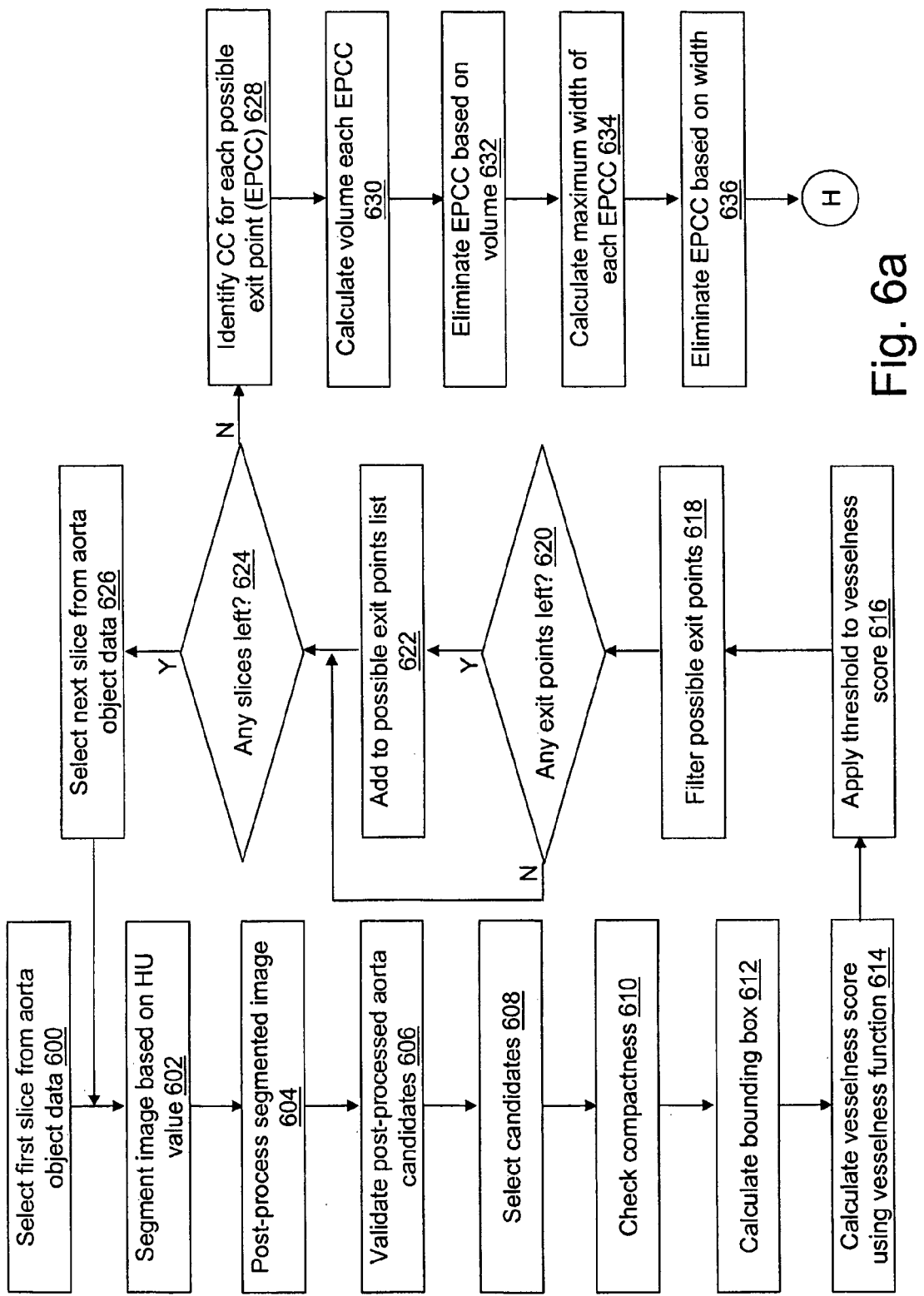

With reference to FIG. 6, exemplary operations associated with identifying the exit points of the coronary arteries from the aorta object are described in accordance with an exemplary embodiment. Additional, fewer, or different operations may be performed, depending on the embodiment. The order of presentation of the operations is not intended to be limiting. Imaging slices including the aorta bounding box and a mask of the aorta detected at a previous slice are processed to detect the aorta at the current slice. In an operation 600, a first slice is selected from the aorta object. In an operation 602, regions are segmented based on a segmentation threshold at the detected aorta edges. The segmentation threshold may be calculated from the median value of pixels of the smoothed image at the detected edges. A ring of pre-defined radius is defined around the aorta edges detected on the previous slice and the edges are found in the ring on the current slice. Small edges are removed from further consideration. The segmentation threshold may be selected adaptively. For example, if no edges are found in the ring using the calculated segmentation threshold, the calculated segmentation threshold is reduced by half, and the procedure is repeated. If no edges are found using the lowered segmentation threshold, the calculated segmentation threshold is used for subsequent slices.

In an operation 604, the segmented image is post-processed. For example, small segmented objects are removed, possible vessels are removed from the segmented aorta candidates, and the segmented aorta candidates are intersected with the aorta detected in the previous slice. In an operation 606, the aorta candidates are validated by ensuring that there is at least one candidate that intersected the aorta detected in the previous slice and by ensuring that the aorta does not grow too fast. For example, if the aorta size in both a previous and a current slice is larger than 1500 pixels, the size growth ratio may be limited to 1.4. In an operation 608, the aorta candidates are selected. For example, CCs with a small intersection with the previously detected aorta are removed from consideration, and the upper-left-most candidate is chosen if a plurality of aorta candidates exist in the current slice. In an operation 610, the compactness of the selected aorta candidate is checked to ensure that the candidate is not compact. If the aorta candidate is not compact, the aorta search window is limited for the next slice. If the aorta candidate is compact, the whole image is used to search for the aorta in the next slice. In an operation 612, a bounding box for the aorta is calculated. If the aorta candidate is not compact, the bounding box size may be fixed and only the position of the bounding box updated to compensate for aorta movement. If the aorta candidate is compact, the bounding box may be attached to the upper left side of the aorta.

In an operation 614, a vesselness score is calculated for each voxel of the aorta object. As known to those skilled in the art, the vesselness score can be determined using a vesselness function. A vesselness function is a widely used function based on the analysis of Hessian eigen values. A good description of an exemplary vesselness function can be found for example in Frangi, A. F., Niessen, W. J., Vincken, K. L. and Viergever, M. A., 1998, "Multiscale Vessel Enhancement Filtering", MICCAI'98, LNCS 1496, pp. 130-137. In an operation 616, a vesselness threshold is applied to the calculated vesselness score to identify possible exit points based on the HU value of a ring around the aorta object. Pixels in a ring around the detected aorta are grouped into CCs, which are analyzed to choose the most probable candidates for coronary tree exit points. In an operation 618, possible exit points are filtered to remove false candidates. For example, the possible exit points may be filtered based on a size of the CC corresponding to the possible exit, a location of the CC relative to the aorta, an incident angle of the CC relative to the aorta, etc. In an operation 620, a determination is made concerning whether or not any exit points are left. If no exit points are left for this slice, processing continues at an operation 624. If one or more exit points are left for this slice, processing continues at an operation 622. In operation 622, the one or more exit points left for this slice are added to a possible exit points list. In an operation 624, a determination is made whether or not the last slice has been processed. If the last slice has not been processed, processing continues at an operation 626. In operation 626, the next slice is selected from the aorta object data and processing continues at operation 602.

If the last slice has been processed, processing continues at an operation 628. In operation 628, a CC is identified for each exit point included in the possible exit points list. In an operation 630, a volume is calculated for each exit point CC (EPCC). In an operation 632, any EPCC having a volume below a volume threshold is eliminated from further consideration as an exit point. For example, the volume threshold may be 1500 voxels. In an operation 634, a maximum width of each EPCC is calculated. In an operation 636, any EPCC having a maximum width below a width threshold is eliminated from further consideration as an exit point. For example, the width threshold may be 2 mm. In an operation 638, a distance to the aorta is calculated for each EPCC. In an operation 640, the EPCC having a minimum distance to the aorta is selected. In an operation 642, a determination is made concerning whether or not a plurality of EPCCs remain. If a plurality of EPCCs remain, processing continues at an operation 644. If a plurality of EPCCs do not remain, processing continues at an operation 646. In operation 644, the EPCC having a maximum width is selected from the plurality of EPCCs remaining. In operation 646, the exit point is identified from the selected EPCCs.

With reference again to FIG. 2, in an operation 242, a coronary artery vessel tree is defined. For a traversed section of the blood vessel tree, a set of end points is identified, and an attempt is made to continue tracking beyond the end point in the direction of the corresponding tree branch. If an additional tree segment is detected, it is connected to the traversed tree, and the processing continues recursively. The process is finished when no branch can be continued. The stopping condition may result in connecting a wrong structure to the coronary tree (e.g. a vein or some debris in a noisy CT study). As a result, the successfully tracked vessels are identified and those which remain to be detected are identified. For example, which blood vessels are to be segmented (e.g. RCA, LM, LAD, LCX and others) may be defined as an input to the process. Additionally, a maximum vessel length to track (e.g. 5 cm from the aorta) and a minimum blood vessel diameter to continue tracking also may be defined as inputs to the process.

The location of some blood vessels may be based on anatomical landmarks. For example, the RCA goes in the right atrioventricular plane. These anatomical landmarks, which may be collated through an anatomical priors processing operation, allow false structures in the "wrong" places to be discarded and support the location of lost branches in the "right" places. A graph representation of the segmented vessel tree can be built from the identified end points and bifurcation points. Graph nodes are the end points and the bifurcation points. The edges are segments of a vessel centerline between the nodes.

Figure 7A:
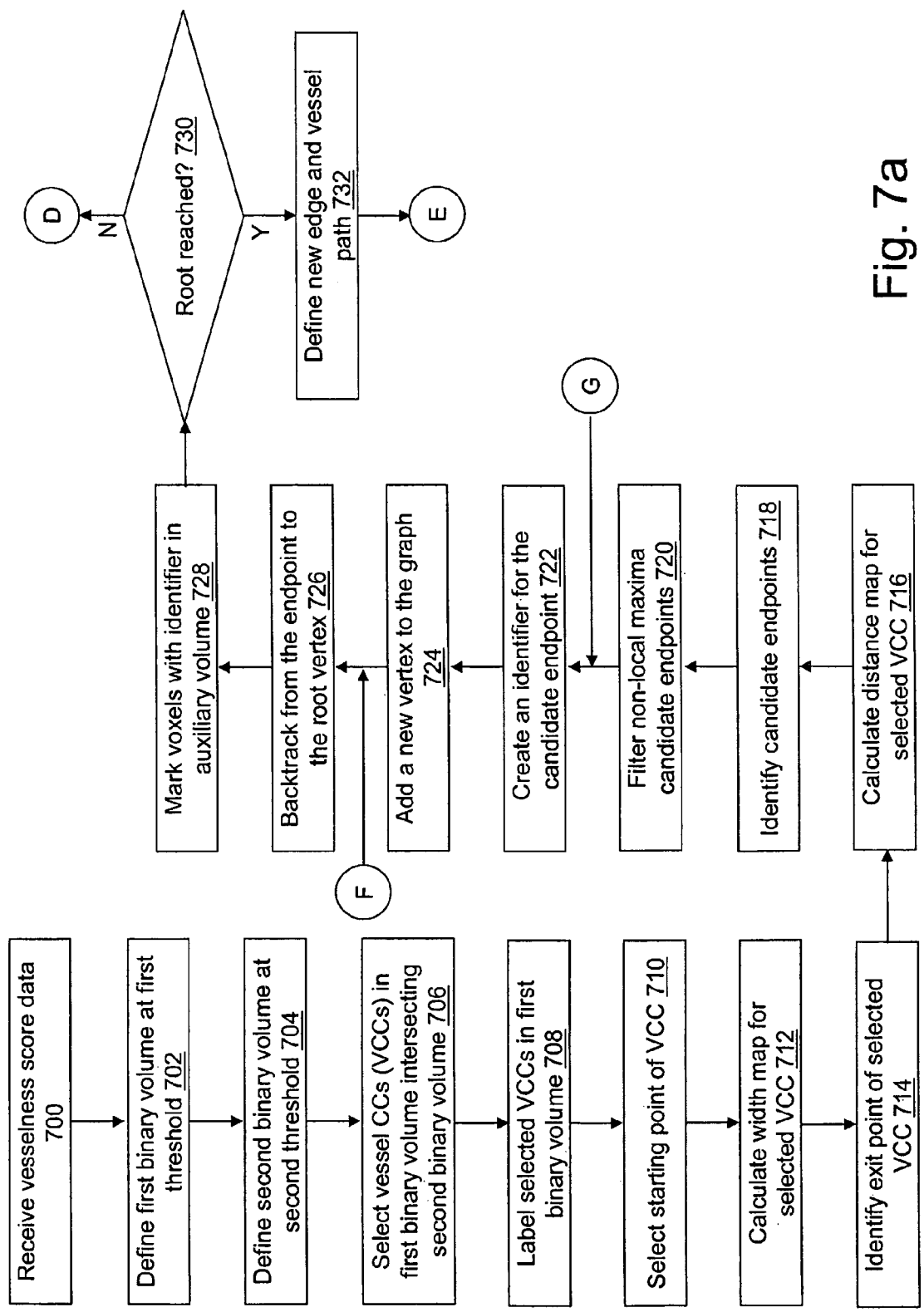
FIGS. 7a and 7b depict a flow diagram illustrating exemplary operations performed in identifying coronary artery vessel tree in accordance with an exemplary embodiment.
Figure 7B:
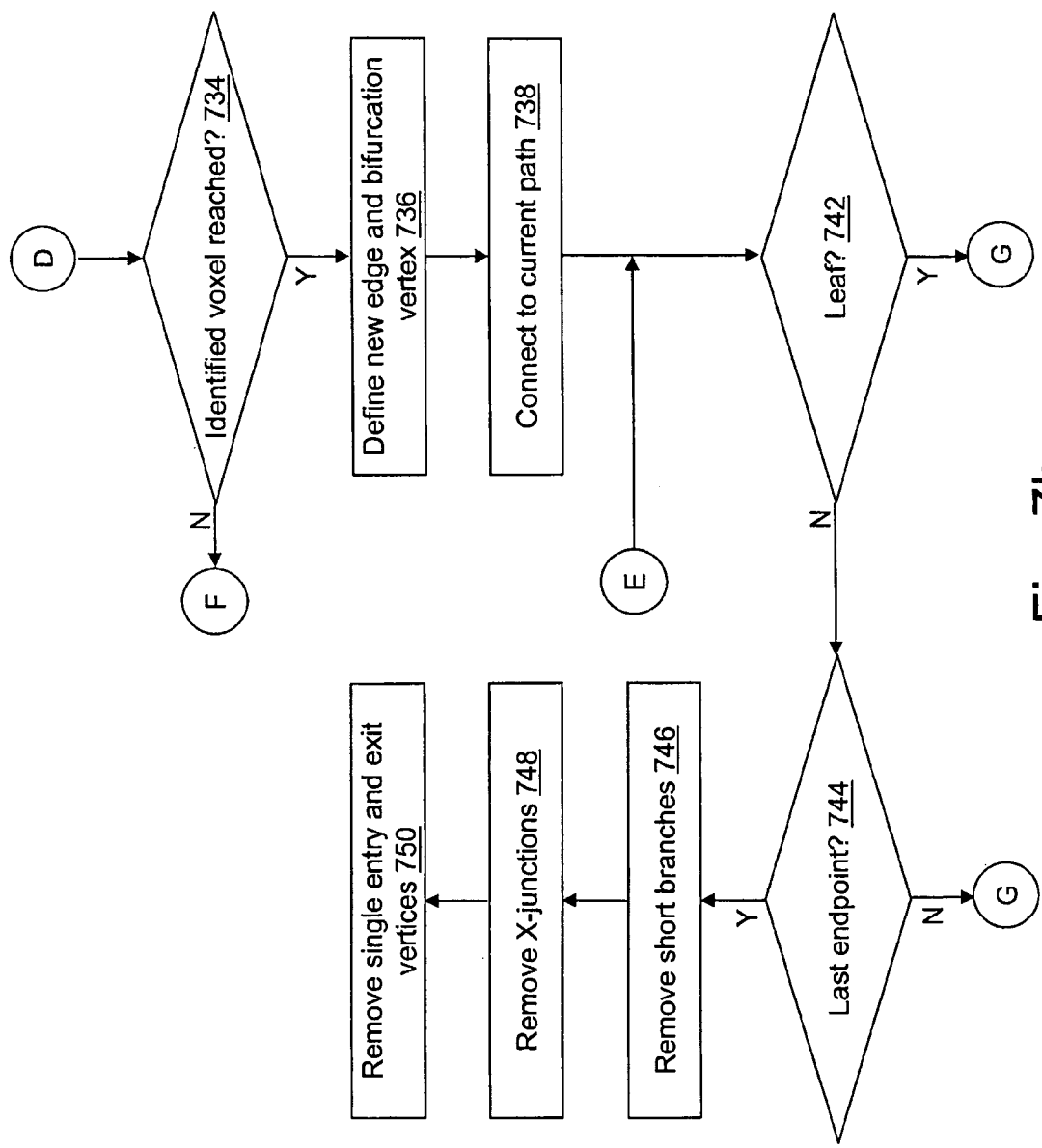

With reference to FIGS. 7a and 7b, exemplary operations associated with defining the coronary artery vessel tree are described in accordance with an exemplary embodiment. Additional, fewer, or different operations may be performed, depending on the embodiment. The order of presentation of the operations is not intended to be limiting. In an operation 700, the vesselness score data is received. In an operation 702, a first binary volume is defined for a first threshold. The first binary volume includes a '1' for each voxel that exceeds the first threshold and a '0' for each voxel that does not exceed the first threshold. In an operation 704, a second binary volume is defined for a second threshold. The second binary volume includes a '1' for each voxel that exceeds the second threshold and a '0' for each voxel that does not exceed the second threshold. The second threshold has a higher HU value than the first threshold. In an operation 706, one or more CCs in the first binary volume that intersect voxels from the second binary volume are selected as the one or more vessel CCs (VCCs). In an exemplary embodiment, intersection may be determined based on a spatial proximity between the CCs. In an exemplary embodiment, the first threshold and the second threshold are selected based on a statistical analysis of the input data such that the amount of voxels above the first threshold is approximately 0.15% of the total number of voxels in the volume and such that the amount of voxels above the second threshold is approximately 0.45% of the total number of voxels.

In an operation 708, the selected VCCs are labeled in the first binary volume. In an operation 710, a starting point or root is selected for a first VCC. In an operation 712, a width map is calculated for the first VCC. The width map includes the width of the VCC or the inverse distance from any point in the VCC to the boundary of the VCC. Thus, small values are near the centerline of the VCC and larger values are at the edges of the VCC. In an operation 714, the exit point of the selected VCC is identified in the binary volume. The right coronary artery tree has a single exit point. Additionally, the left main artery tree has a single exit point. In an operation 716, a distance map is calculated for the first VCC. The distance is calculated from any point in the VCC to the identified exit point. The distance map includes the calculated distance weighted by the width to ensure that the minimal path follows the vessel centerline. In an operation 718, candidate endpoints are identified. For example, during the calculation of the weighted distance map, one or more candidate endpoints may be saved. The candidate endpoints are voxels, which did not update any of their neighbors during the distance map calculation. In an operation 720, non-local maxima candidate endpoints are filtered. Thus, the candidate endpoints are scanned and only local maxima with respect to the distance from the root over a given window are kept. This process eliminates candidates that are not true blob vessel end points.

In an operation 722, an identifier for the candidate endpoint is created. In an operation 724, a new vertex is added to a symbolic graph of the vessel tree. In an operation 726, a first candidate endpoint is backtracked to the root to create graph edges. An auxiliary volume is used to mark voxels that have already been visited. The back-tracking may be a gradient descent iterative process (the gradient is in the distance field). Because the weighted distance map contains a single global minimum (the root), convergence is guaranteed. The method used to define the distance map ensures that the backtracking will be along the centerline or close to it. In an operation 728, all visited voxels in the auxiliary volume are marked with the current vertex identifier during the backtracking.

In an operation 730, a determination is made concerning whether or not a root is reached. If a root is reached, processing continues at an operation 732. If a root is not reached, processing continues at an operation 734. In operation 732, a new edge and vessel path are defined based on the backtracking. Processing continues at an operation 740. In an operation 734, a determination is made concerning whether or not an already visited voxel is reached. If an already visited voxel is reached, processing continues at an operation 736. If an already visited voxel is not reached, processing continues at an operation 726 to continue the backtracking to the endpoint. In an operation 736, a new edge and a new bifurcation vertex are defined. In an operation 738, the new bifurcation vertex is connected to the currently backtracked path, and the new edge and the new bifurcation vertex are added to the vessel tree.

In an operation 742, a determination is made concerning whether or not the endpoint is a leaf of the vessel tree or a vessel disconnected due to a low vesselness measure. In an exemplary embodiment, the determination is made based on the direction of the vessel at the endpoint and by searching for another VCC in a vacancy that contains a nearby endpoint. If the endpoint is a leaf, processing continues at operation 722 to create a new graph. The two graphs are joined together. If the endpoint is not a leaf, processing continues at an operation 744. In an operation 744, a determination is made concerning whether or not the last endpoint has been processed. If the last endpoint has not been processed, processing continues at operation 722.

If the last endpoint has been processed, processing continues at an operation 746. In operation 746, short branches are removed based on the rationale that they do not contribute to the analysis because important findings are usually located at the major blood vessels, which are thick and elongated. Therefore, in an exemplary embodiment, graph edges which lead to endpoints that are less than a length threshold are removed. An exemplary length threshold is 5 mm. In an operation 748, x-junctions are removed to eliminate veins. Veins are usually faint and spatially close to the arteries. X-junctions are defined as two very close bifurcation points. For example, close bifurcation points may be less than approximately 3 mm from each other. In an exemplary embodiment, a bifurcation may be two VCCs intersecting at angles between approximately 70 degrees and approximately 110 degrees. Additionally, a bifurcation may be two VCCs intersecting at angles approximately equal to 90 degrees. The sub-tree which remains is the one which has the closest direction to the edge arriving from the aorta.

Figure 10:
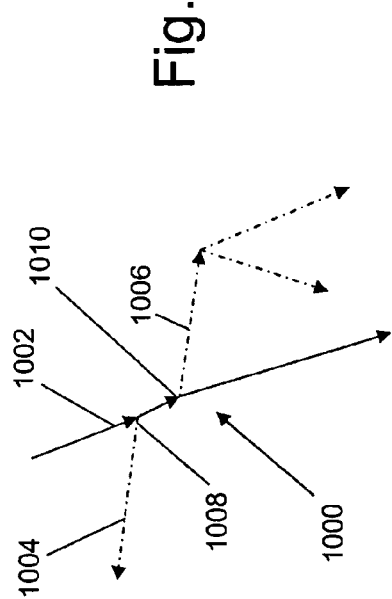
FIG. 10 depicts a graph illustrating X-junction removal from a coronary artery vessel tree in accordance with an exemplary embodiment.

For example, with reference to FIG. 10, a vessel tree 1000 includes a first vessel path 1002, a second vessel path 1004, and a third vessel path 1006. First vessel path 1002 and second vessel path 1004 form a first x-junction 1008. First vessel path 1002 has the closest direction to the edge arriving from the aorta and is selected to remain in the vessel tree. Second vessel path 1004 is removed. First vessel path 1002 and third vessel path 1004 form a second x-junction 1010. Again, first vessel path 1002 has the closest direction to the edge arriving from the aorta and is selected to remain in the vessel tree. Third vessel path 1006 is removed. In an operation 750, single entry, single exit point vertices are removed. These vertices are created when one of the endpoints is recursively continued. The vertex is removed, and the two edges are joined to a single path.

With reference again to FIG. 2, in an operation 244, the defined coronary artery vessel tree is labeled. A list of graph edges (vessel segments) may be assigned to each blood vessel tracked by analyzing the relative section positions and locations relative to detected anatomical heart landmarks. The blood vessel tree represented by a centerline for each blood vessel segment is stored at computing device 102.

In an operation 246, a radius of each blood vessel is determined. In an operation 248, a blood vessel centerline is determined. "Sausages" of blood vessels are obtained from the coronary artery vessel tree. Each "sausage" includes axial blood vessel cross-sections taken perpendicular to the blood vessel direction. Initially, a blood vessel center is presumed to be at the center of each section. Either "stretched" or "curved" blood vessels can be used. Any blood vessel radius and center line estimation method can be used. In an exemplary embodiment, low pass post-filtering between consecutive cross-sections is performed. Because a blood vessel may be surrounded by tissue having similar attenuation values, indirect indicators may be used to define the blood vessel edge. Areas having low values, which clearly don't belong to a blood vessel are identified, and the largest circle that lies outside the identified areas is defined. In an alternative embodiment, a largest circle that can be defined that fits into the valid (bright) area is defined. An arbitration process may be used to determine which approach should be used for each blood vessel. A blood vessel center consisting of a number of pixels can be defined, in particular when a cross section is elongated. In an exemplary embodiment, the blood vessel center is reduced to a single pixel.

Figure 8:
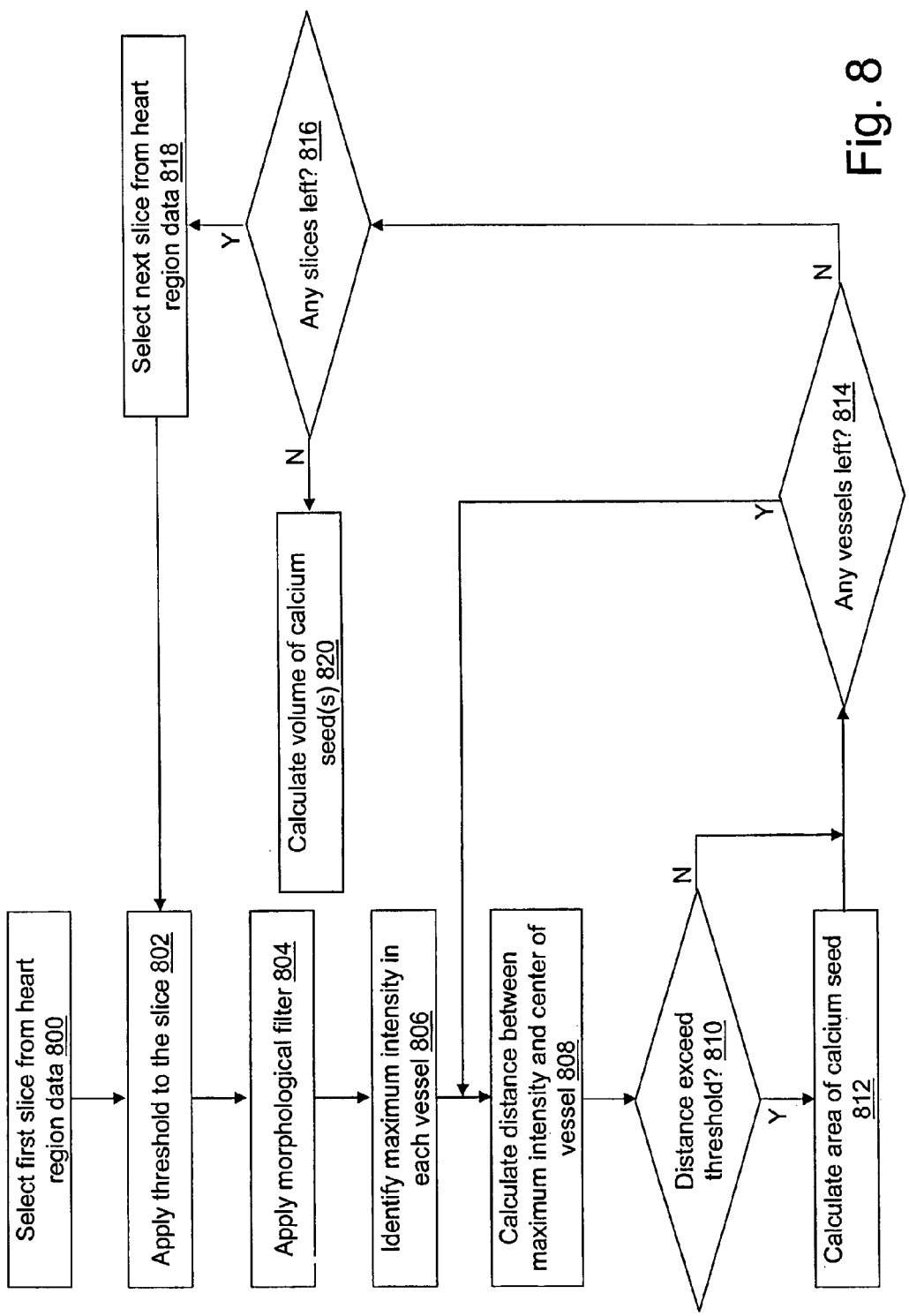
FIG. 8 depicts a flow diagram illustrating exemplary operations performed in identifying calcium seed in accordance with an exemplary embodiment.

In an operation 250, areas of calcium are identified in each blood vessel. Any high precision calcium identification method can be used. In an exemplary embodiment, a cross section based analysis aimed at location of the calcium seeds is performed, and a volume based analysis aimed at removal of spurious seeds created by the "salt noise" and by the growing of valid seeds into the correct calcium area is performed. With reference to FIG. 8, exemplary operations associated with identifying the areas of calcium, if any, in each blood vessel are described in accordance with an exemplary embodiment. Additional, fewer, or different operations may be performed, depending on the embodiment. The order of presentation of the operations is not intended to be limiting. In an operation 800, a first slice is selected from the heart region data. In an operation 802, a calcium threshold is applied to the first slice. In an exemplary embodiment, the calcium threshold is 150 intensity levels above the blood vessel lumen level. Adaptive threshold values taking into account expected lumen values are used. In an operation 804, a morphological filter is applied to the thresholded first slice based on the non-concentric nature of the calcium deposits. Empirical observations indicate that calcium tends to appear close to the blood vessel borders.

In an operation 806, a maximum intensity in a given cross-section is identified as a possible location of a Calcium seed. In an operation 808, a distance from the center to the maximum intensity is calculated. In an operation 810, a determination is made concerning whether or not the calculated distance exceeds a calcium distance threshold. The calcium distance threshold is based on a comparison with an estimated radius value. If the distance does not exceed the calcium distance threshold, processing continues in an operation 814. If the distance does exceed the calcium distance threshold, processing continues in an operation 812. In operation 812, an area of the calcium seed is calculated. In operation 814, a determination is made concerning whether or not any vessels remain for processing. If vessels remain, processing continues at operation 808. If no vessels remain, processing continues at an operation 816. In operation 816, a determination concerning whether or not any slices remain for processing is performed. If no slices remain, processing continues at an operation 820. If slices remain, processing continues at an operation 818. In operation 818, the next slice is selected from the heart region data and processing continues at operation 802. In operation 820, a volume of any identified calcium seed(s) is calculated based on the area calculated for each slice and the number of slices over which the identified calcium seed(s) extends. If a calcium seed is identified, it also is extended to the surrounding high intensity areas providing that no "spill to the center" occurs. An extent of the calcium seed may be determined based on a threshold. For example, lumen intensities exceeding approximately 650 HU may be considered to be calcified plaque or part of the Calcium seed.

Figure 9:
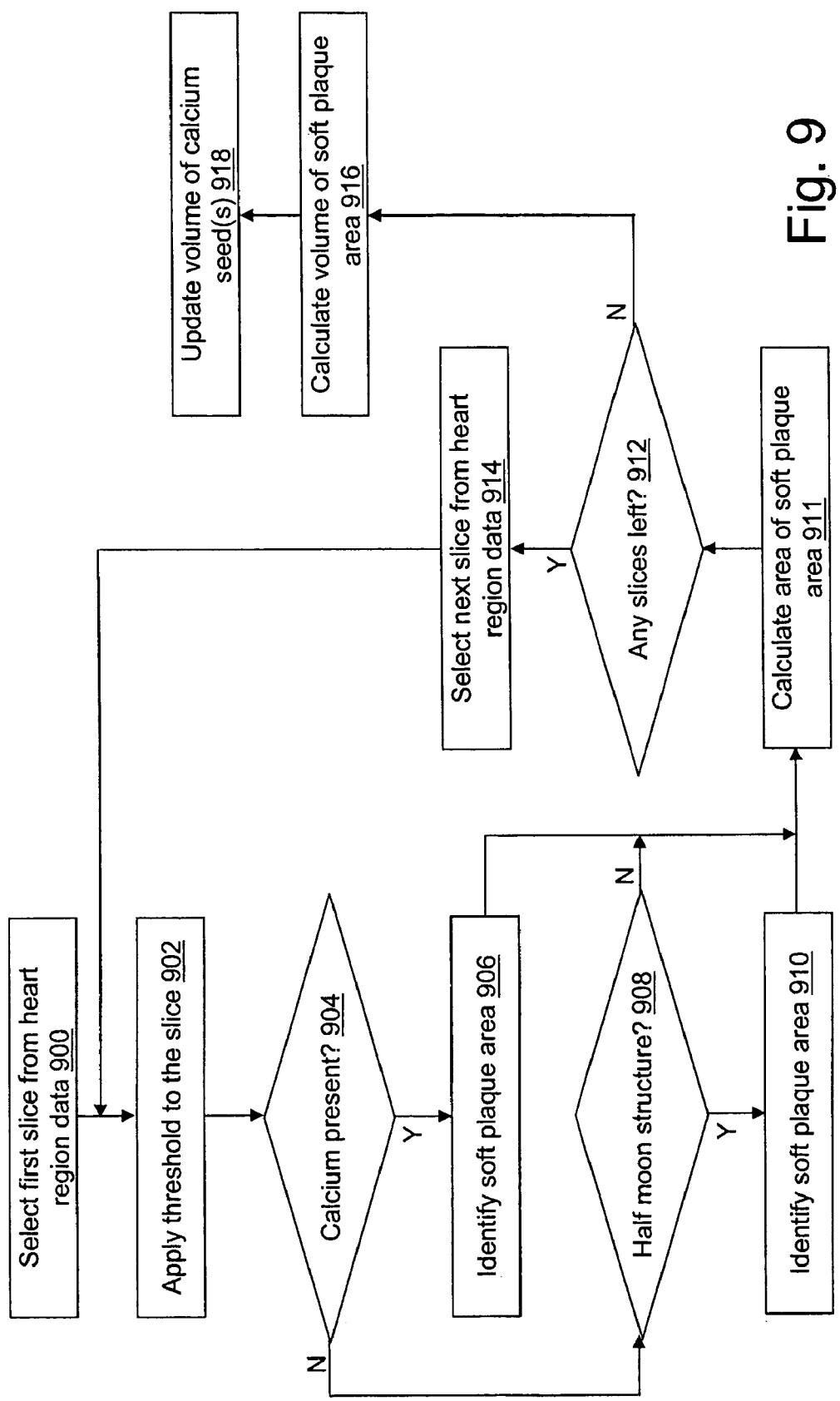
FIG. 9 depicts a flow diagram illustrating exemplary operations performed in identifying in identifying soft plaque in accordance with an exemplary embodiment.

With reference again to FIG. 2, in an operation 252, areas of soft plaque are identified in each blood vessel by the low intensity inside the blood vessel area. Any high precision soft plaque identification method can be used. With reference to FIG. 9, exemplary operations associated with identifying the areas of soft plaque, if any, in each blood vessel are described in accordance with an exemplary embodiment. Additional, fewer, or different operations may be performed, depending on the embodiment. The order of presentation of the operations is not intended to be limiting. In an operation 900, a first slice is selected from the heart region data. In an operation 902, a soft plaque threshold is applied to the first slice. In an exemplary embodiment, the soft plaque threshold is between approximately 50 HU and approximately 200 HU. Adaptive threshold values taking into account expected lumen values are used in an exemplary embodiment. In an operation 904, a determination is made concerning whether or not calcium is present. The presence of calcium may indicate the presence of the frequent figure "8" shaped pattern. In the figure "8" shaped pattern, calcium is located in one of the ovals of the "8". A lumen is located in the other oval of the "8", and soft plaque connects the two ovals. If calcium is present, processing continues at an operation 906. If calcium is not present, processing continues at an operation 908. In operation 906, a soft plaque area is identified and processing continues at an operation 911.

In operation 908, a determination is made concerning whether or not a half-moon structure is located in the blood vessel lumen. If a half-moon structure is identified from the determination, processing continues at an operation 910. If a half-moon structure is not identified from the determination, processing continue at operation 911. In operation 910, a soft plaque area is identified. In operation 911, an area of the identified soft plaque is calculated. In operation 912, a determination concerning whether or not any slices remain for processing is performed. If no slices remain, processing continues at an operation 916. If slices remain, processing continues at an operation 914. In operation 914, the next slice is selected from the heart region data, and processing continues at operation 902. In operation 916, a volume of any identified soft plaque area(s) is calculated based on the area calculated for each slice and the number of slices over which the identified soft plaque area(s) extends. In an operation 918, a volume of any identified calcium seed(s) is updated to include areas between the calcium seed and the blood vessel border and between the calcium and soft plaque areas to compensate for natural intensity low passing that may have occurred during the CT image acquisition.

With reference again to FIG. 2, in an operation 254, a severity of any obstructions identified containing soft plaque or calcium is calculated. Any obstruction computation method can be used. In an exemplary embodiment, a total obstruction ratio is calculated as a ratio of the total calcium and soft plaque areas divided by the total blood vessel area excluding the border area. In an exemplary embodiment, an obstruction is identified to be severe if the total obstruction ratio exceeds 50% for at least two consecutive cross sections. An examining physician may be allowed to control the threshold to achieve a system sensitivity matching their clinical requirements.

In some pathological cases, the cross section images may appear reasonably normal. In these cases, pathology must be identified based on the analysis of global variations. In an operation 256, global filters are applied to identify pathologies. For example, a first filter may be applied to identify a rapid decrease in the blood vessel radius. A second filter may be applied to identify a rapid decrease in the lumen intensity. A third filter may be applied to identify a rapid increase in the lumen intensity. The decisions from the series of filters may be cumulative. As a result, it is sufficient if a pathology is identified through use of one of the three filters. The filters may use the values of blood vessel radius and luminance as computed above. Use of the global filters takes into account that even healthy vessels feature significant radius and luminance variations in particular due to natural narrowing of the blood vessels, rapid changes in the vicinity of bifurcations (especially after the bifurcations), noise (in particular for relatively narrow vessels), etc. Anomalies identified by the global filters are discarded, if located in the vicinity of any bifurcations.

The operations described with reference to FIGS. 2-9 have been applied to a set of 50 clinical patient studies. The same studies were analyzed by expert radiologists. Overall, 200 blood vessels were analyzed. Out of this benchmark, 42 cases were identified as having severe pathologies. The remaining 158 cases were deemed to have no pathologies or only moderate pathologies. Pathology identification application 112 identified all of the severe cases correctly with a false alarm rate of 11%.

Figure 11:
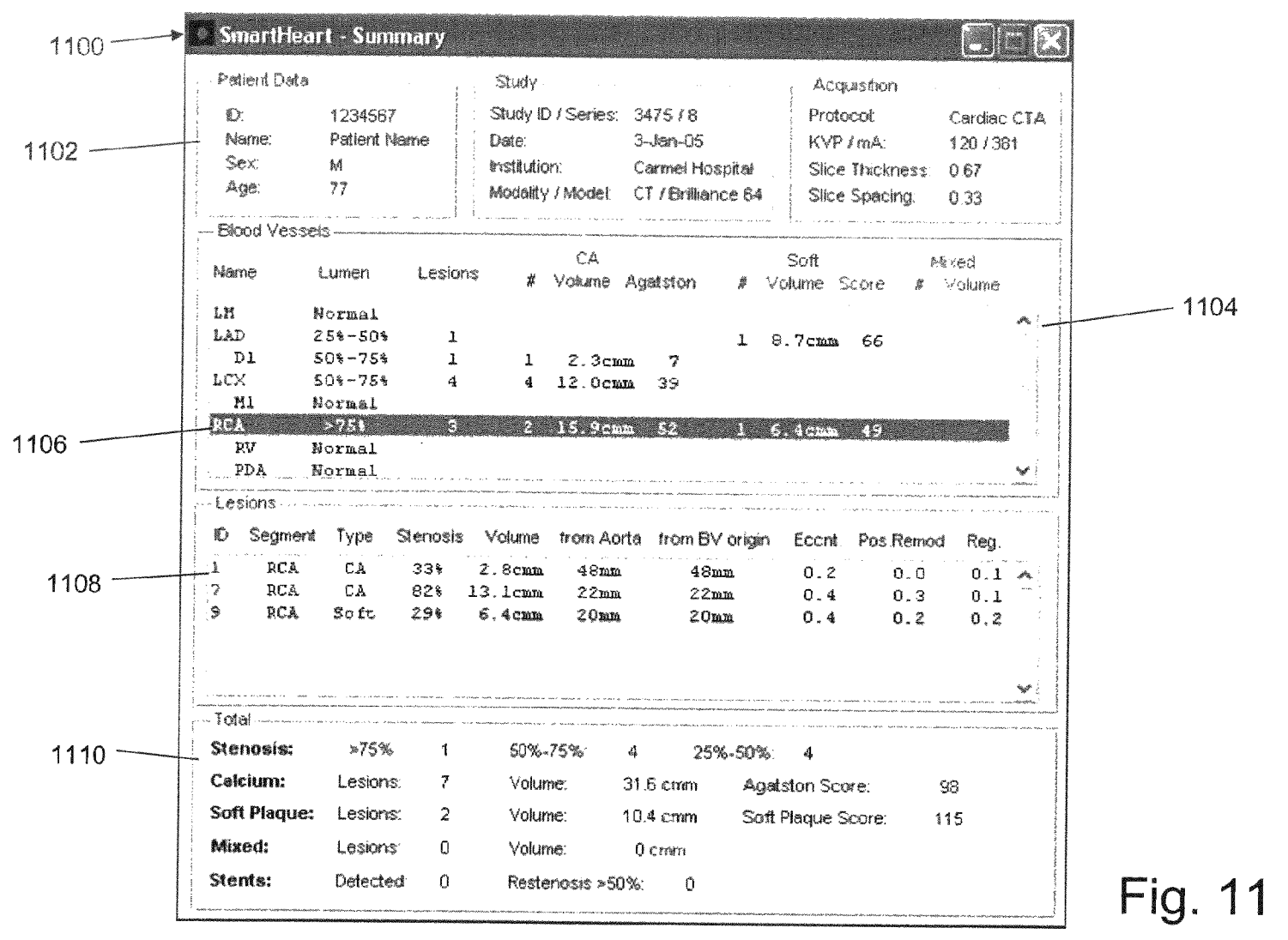

With reference again to FIG. 2, in an operation 258, a summary report is provided to a user based on the processes described with reference to FIGS. 2-9. With reference to FIG. 11, a first user interface 1100 of visualization application 114 is shown. First user interface 1100 may include a header portion 1102. Header portion 1102 may include patient data, study data, and/or acquisition data. For example, data displayed in header portion 1102 may be obtained from a header of the DICOM data. First user interface 1100 further may include a blood vessel list portion 1104. Blood vessel list portion 1104 may include a list of the blood vessels in the created blood vessel tree. Displayed next to a name identifying each blood vessel may be information related to each blood vessel including a lumen status, a total number of lesions, a number of calcium lesions, and a number of soft plaque lesions. The lumen status may indicate "normal" or a percentage of blockage that may be a percentage range. If a plurality of lesions are present, the range may indicate the maximum blockage range. A maximum volume and Agatston score may be displayed for the calcium lesions. A maximum volume and score also may be displayed for the soft plaque lesions.

User selection of a blood vessel 1106 in blood vessel list portion 1104 may cause display of a detailed description of the lesions associated with the selected blood vessel in a detail portion 1108. Detail portion 1108 may include a list of the lesions. For each lesion, a segment name, a lesion type, a degree of stenosis value, a volume, a distance from the aorta, a distance from the blood vessel origin, an eccentricity, a degree of positive remodeling, and a morphological regularity may be shown. First user interface 1100 further may include a totals portion 1110. Totals portion 1110 may include summary data associated with a degree of stenosis, lesions, the number of stents, etc.

Figure 12:
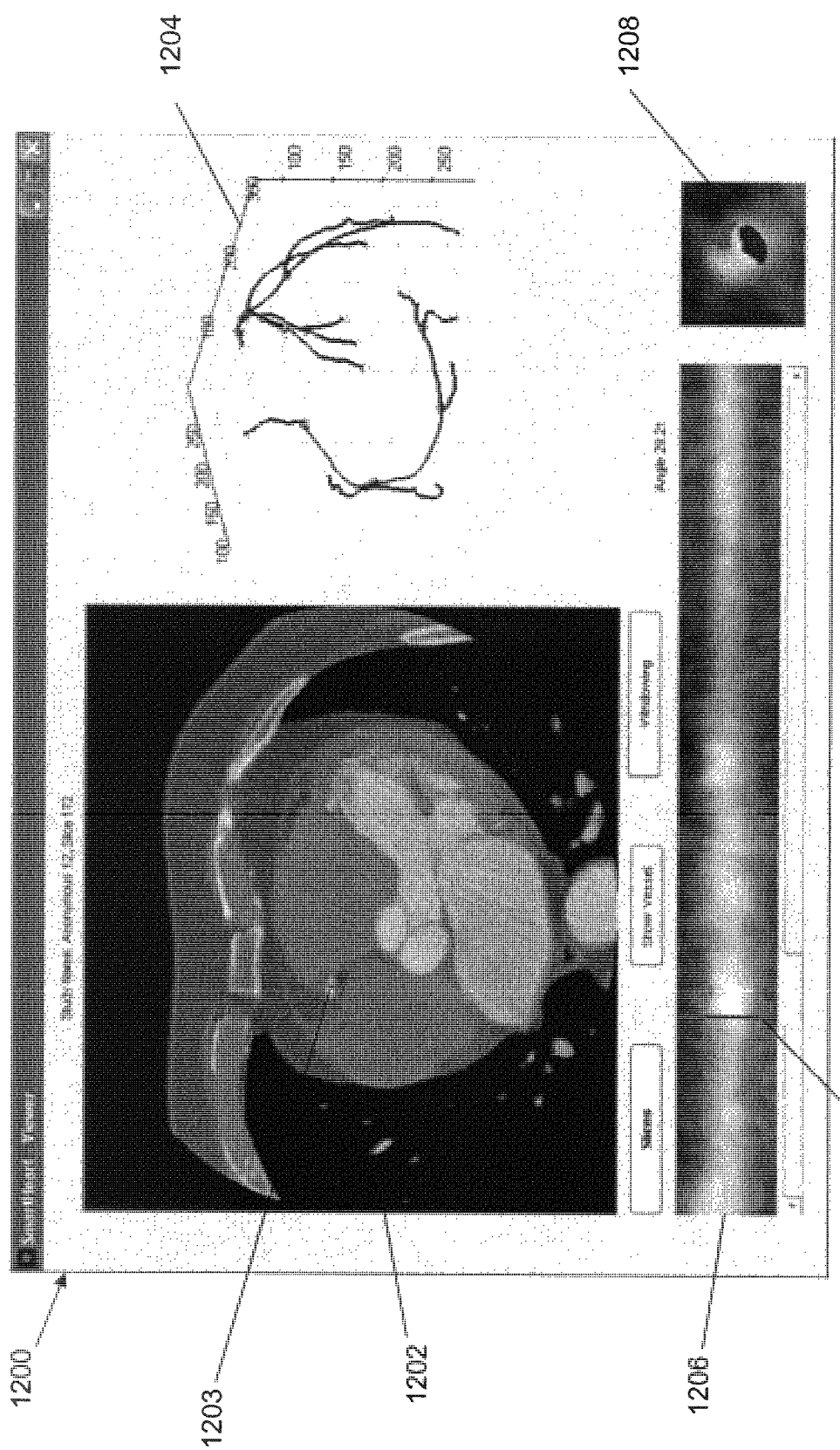
FIG. 12 depicts a second user interface of the visualization application presenting multiple views of a pathology in accordance with a first exemplary embodiment.

With reference again to FIG. 2, in an operation 260, a visualization of the blood vessels is provided to a user based on the processes described with reference to FIGS. 2-9. With reference to FIG. 12, a second user interface 1200 of visualization application 114 in accordance with a first exemplary embodiment is shown. In the exemplary embodiment of FIG. 12, four simultaneous views of the same pathology may be shown to facilitate a correct diagnosis with each view presented in a different area of second user interface 1200. Each view may be created using a variety of graphical user interface techniques in a common window, in separate windows, or in any combination of windows. Second user interface 1200 may include a first axial slice viewer 1202, a first 3-D coronary vessel map 1204, a first stretched blood vessel image 1206, and an intra-vascular ultrasound (IVUS) type view 1208. First axial slice viewer 1202 presents intensity levels from a slice of imaging data. The intensity levels may be indicated in color or gray-scale. For example, first axial slice viewer 1202 may indicate an identified pathology 1203 in red. First axial slice viewer 1202 may present the slice of imaging data in a top left area of second user interface 1200.

First 3-D coronary vessel map 1204 provides a view of the blood vessel tree synchronized with first axial slice viewer 1202 to indicate the identified pathology 1203. First 3-D coronary vessel map 1204 may be presented in a top right area of second user interface 1200 and may include a 3-D grid to identify the length of the blood vessels in the blood vessel tree in each direction. Selecting an area of first stretched blood vessel image 1206 may cause image rotation of first 3-D coronary vessel map 1204 around its axis to facilitate a correct 3-D perception of the blood vessel structure. First 3-D coronary vessel map 1204 may be synchronized with first axial slice viewer 1202 to distinguish the selected blood vessel from the remaining blood vessels in the blood vessel tree. First 3-D coronary vessel map 1204 may be rotated using an input interface as known to those skilled in the art. Indicators may be provided in first 3-D coronary vessel map 1204 to indicate end points and bifurcations. For example, end points may be indicated using green circles and bifurcations may be indicated using red circles.

First stretched blood vessel image 1206 includes a vertical bar which denotes a location of the slice displayed in first axial slice viewer 1202 in a stretched view of a selected blood vessel. First stretched blood vessel image 1206 may be located in a bottom left area of second user interface 1200. The physician can superimpose corresponding plaque areas. For example, soft plaque may be indicated in red and calcified plaque indicated in blue. If desired, the physician can invoke an edit mode and correct automatic results.

Figure 13:
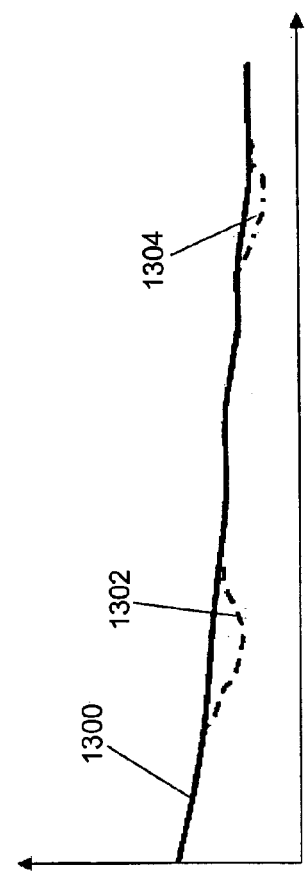
FIG. 13 depicts a third user interface of the visualization application presenting a blood vessel effective lumen area as a function of distance from the aorta in accordance with an exemplary embodiment.

With reference to FIG. 13, a third user interface of visualization application 114 graphically displays a lumen area of each blood vessel to clearly identify all stenosis lesions and to allow an evaluation of their severity. The graphical display includes a distance from the aorta on the X-axis and a lumen area on the Y-axis. A first curve 1300 indicates a normal blood vessel lumen. A second curve 1302 indicates a stenosis due to calcified plaque. A third curve 1304 indicates a stenosis due to soft plaque.

Figure 14:
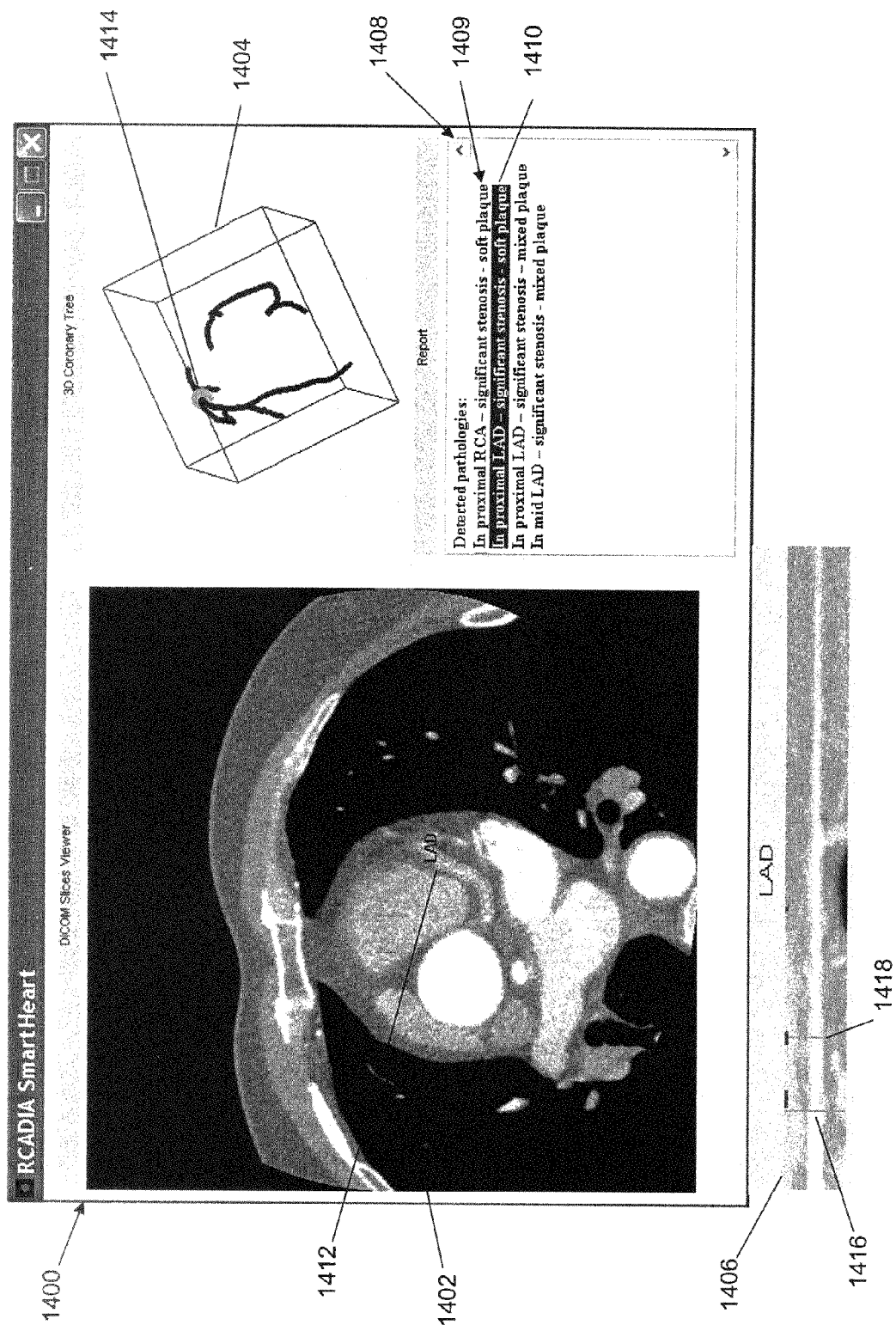
FIG. 14 depicts a fourth user interface of the visualization application presenting multiple views of a pathology in accordance with a second exemplary embodiment.

With reference to FIG. 14, a fourth user interface 1400 of visualization application 114 in accordance with a second exemplary embodiment is shown. Fourth user interface 1400 may include a second axial slice viewer 1402, a second 3-D coronary vessel map 1404, a second stretched blood vessel image 1406, and a pathology report type view 1408. Second axial slice viewer 1402 may include an axial slice of the imaging data presented in a top left area of second user interface 1400. provides a current location on the 3-D coronary vessel map synchronized with second axial slice viewer 1402. Second 3-D coronary vessel map 1404 may be presented in a top right area of second user interface 1400 and may include a 3-D grid to identify the length of the blood vessels in the blood vessel tree in each direction. Selecting an area of second 3-D coronary vessel map 1404 may cause image rotation around its axis facilitating a correct 3-D perception of the blood vessel structure.

Second stretched blood vessel image 1406 includes a vertical bar which denotes a location of the slice displayed in second axial slice viewer 1402 in a stretched view of a selected blood vessel. Second stretched blood vessel image 1406 may be presented in a bottom left area of second user interface 1400.

Pathology report type view 1408 may contain a pathology list 1409 of detected pathologies based on the processes described with reference to FIGS. 2-9. The pathologies may include soft plaque, calcified plaque, and mixed plaque regions. The location and stenosis level may be included for each pathology in pathology list 1409. Selecting a pathology 1410 from pathology list 1409 of pathology report type view 1408 may cause a synchronized display of pathology 1410 in second axial slice viewer 1402, second 3-D coronary vessel map 1404, and second stretched blood vessel image 1406. For example, second axial slice viewer 1402 includes a first pathology indicator 1412, which indicates the location of pathology 1410 in second axial slice viewer 1402. Second 3-D coronary vessel map 1404 includes a second pathology indicator 1414, which indicates the location of pathology 1410 in the 3-D coronary artery tree view. Second stretched blood vessel image 1406 includes a first point 1416 and a second point 1418, which indicate the location of pathology 1410 in second stretched blood vessel image 1406.

With reference to FIG. 15, a fifth user interface 1500 of visualization application 114 in accordance with a third exemplary embodiment is shown. Fifth user interface 1500 may include a third axial slice viewer 1502 and a third stretched blood vessel image 1504. Third axial slice viewer 1502 is synchronized with third stretched blood vessel image 1504. Third axial slice 1502 presents intensity levels from an axial slice of imaging data. The intensity levels may be indicated in color or gray-scale. For example, third axial slice viewer 1502 may indicate an identified pathology 1506 in red. Third stretched blood vessel image 1504 presents intensity levels of a blood vessel selected from third axial slice viewer 1502 and shown in stretched form. Third stretched blood vessel image 1504 may includes a vertical bar 1508 which denotes a location of the slice presented in third axial slice viewer 1502. When the user selects a vessel area in third axial slice viewer 1502, third stretched blood vessel image 1504 shows a stretched presentation of the appropriate vessel. When the user selects an area in third stretched blood vessel image 1504, third axial slice viewer 1502 displays the appropriate slice of the patient study.

In an exemplary embodiment, fifth user interface 1500 may initially include third axial slice viewer 1502. When the user selects an artery from third axial slice viewer 1502, the selected blood vessel is presented in third stretched blood vessel image 1504 with vertical bar 1508 denoting the location of the slice presented in third axial slice viewer 1502. Execution of one or more of the processes described with reference to FIGS. 2-9 may be performed after selection of the blood vessel to identify the stretched blood vessel presented in third stretched blood vessel image 1504. As a result, using a single "click" the user may trigger a determination of all relevant segments of the blood vessel from the slices and reconstruct the stretched blood vessel for presentation in third stretched blood vessel image 1504.

Fifth user interface 1500 further may include an axial presentation only button 1510, a new study selection button 1512, a save current screen button 1514, and an exit program button 1516. User selection of axial presentation only button 1510 causes stretched blood vessel image 1504 to be removed from fifth user interface 1500. User selection of new study selection button 1512 causes presentation of a selection window that allows the user to select a new patient study for analysis. User selection of save current screen button 1514 causes presentation of a save window that allows the user to select a location and a name for a file to which the contents of fifth user interface 1500 are saved for review, for printing, for sending with a message, etc. User selection of exit program button 1516 may cause fifth user interface 1500 to close.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The functionality described may be implemented in a single executable or application or may be distributed among modules that differ in number and distribution of functionality from those described herein. Additionally, the order of execution of the functions may be changed depending on the embodiment. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of presenting information associated with a blood vessel to a user for assessment of the blood vessel, the method comprising:

presenting a two-dimensional slice of three-dimensional imaging data of a blood vessel to a user in a first user interface;

receiving a blood vessel selection from the user, wherein the user selects the blood vessel through an interaction with the first user interface;

identifying a blood vessel path associated with the received blood vessel selection from the three-dimensional imaging data;

presenting an intensity of the selected blood vessel along the identified blood vessel path to the user for analysis of the selected blood vessel;

receiving imaging data including a heart region, a pulmonary artery region, an ascending aorta region, and a thoraco-abdominal aorta region of a patient;

identifying the heart region from the imaging data;

analyzing the identified heart region to detect a coronary pathology;
identifying an ascending aorta object from the ascending aorta region of the imaging data;
analyzing the identified ascending aorta object to detect an aortic dissection;
identifying an abdominal aorta object from the thoraco-abdominal aorta region;
analyzing the identified abdominal aorta object to detect an aortic dissection;
identifying a left main pulmonary artery object and a right main pulmonary artery object from the pulmonary artery region of the imaging data;
analyzing the identified left main pulmonary artery object and the identified right main pulmonary artery object to detect a pulmonary embolism; and
generating a report including any detected coronary pathology, any detected aortic dissection, and any detected pulmonary embolism,
wherein identifying the heart region comprises:
projecting the received imaging data into a first plane of three dimensions of the received imaging data;
applying a first threshold to the first plane of data, wherein the first threshold is selected to eliminate a first pixel associated with air;
identifying a largest first connected component from the first threshold applied data;
calculating a first center of mass of the identified largest first connected component to define a first coordinate and a second coordinate;
projecting the received imaging data into a second plane of the three dimensions, wherein the second plane is perpendicular to the first plane;
applying a second threshold to the second plane of data, wherein the second threshold is selected to eliminate a second pixel associated with air;
identifying a largest second connected component from the second threshold applied data; and
calculating a second center of mass of the identified largest second connected component to define a third coordinate;
wherein a center of a heart region is defined from the defined first coordinate, the defined second coordinate, and the defined third coordinate; and
further wherein the heart region has a width in each of the three dimensions.

2. A system for presenting information associated with a blood vessel to a user for assessment of the blood vessel, the system comprising:
an imaging apparatus configured to generate imaging data of a patient; and
a processor operably coupled to the imaging apparatus to receive the generated imaging data, the processor configured to:
present a two-dimensional slice of three-dimensional imaging data of a blood vessel to a user in a first user interface;
receive a blood vessel selection from the user, wherein the user selects the blood vessel through an interaction with the first user interface;
identify a blood vessel path associated with the received blood vessel selection from the three-dimensional imaging data;
present an intensity of the selected blood vessel along the identified blood vessel path to the user for analysis of the selected blood vessel;
receive imaging data including a heart region, a pulmonary artery region, an ascending aorta region, and a thoraco-abdominal aorta region of a patient;
identify the heart region from the imaging data;
analyze the identified heart region to detect a coronary pathology;
identify an ascending aorta object from the ascending aorta region of the imaging data;
analyze the identified ascending aorta object to detect an aortic dissection;
identify an abdominal aorta object from the thoraco-abdominal aorta region;
analyze the identified abdominal aorta object to detect an aortic dissection;
identify a left main pulmonary artery object and a right main pulmonary artery object from the pulmonary artery region of the imaging data;
analyze the identified left main pulmonary artery object and the identified right main pulmonary artery object to detect a pulmonary embolism; and
generate a report including any detected coronary pathology, any detected aortic dissection, and any detected pulmonary embolism,
wherein the heart region is identified by:
projecting the received imaging data into a first plane of three dimensions of the received imaging data;
applying a first threshold to the first plane of data, wherein the first threshold is selected to eliminate a first pixel associated with air;
identifying a largest first connected component from the first threshold applied data;
calculating a first center of mass of the identified largest first connected component to define a first coordinate and a second coordinate;
projecting the received imaging data into a second plane of the three dimensions, wherein the second plane is perpendicular to the first plane;
applying a second threshold to the second plane of data, wherein the second threshold is selected to eliminate a second pixel associated with air;
identifying a largest second connected component from the second threshold applied data; and
calculating a second center of mass of the identified largest second connected component to define a third coordinate;
wherein a center of a heart region is defined from the defined first coordinate, the defined second coordinate, and the defined third coordinate; and
further wherein the heart region has a width in each of the three dimensions.

3. A non-transitory computer-readable storage medium comprising computer-readable instructions to present information associated with a blood vessel to a user for assessment of the blood vessel, the instructions comprising:
presenting a two-dimensional slice of three-dimensional imaging data of a blood vessel to a user in a first user interface;
receiving a blood vessel selection from the user, wherein the user selects the blood vessel through an interaction with the first user interface;
identifying a blood vessel path associated with the received blood vessel selection from the three-dimensional imaging data;
presenting an intensity of the selected blood vessel along the identified blood vessel path to the user for analysis of the selected blood vessel;

receiving imaging data including a heart region, a pulmonary artery region, an ascending aorta region, and a thoraco-abdominal aorta region of a patient;
identifying the heart region from the imaging data;
analyzing the identified heart region to detect a coronary pathology;
identifying an ascending aorta object from the ascending aorta region of the imaging data;
analyzing the identified ascending aorta object to detect an aortic dissection;
identifying an abdominal aorta object from the thoraco-abdominal aorta region;
analyzing the identified abdominal aorta object to detect an aortic dissection;
identifying a left main pulmonary artery object and a right main pulmonary artery object from the pulmonary artery region of the imaging data;
analyzing the identified left main pulmonary artery object and the identified right main pulmonary artery object to detect a pulmonary embolism; and
generating a report including any detected coronary pathology, any detected aortic dissection, and any detected pulmonary embolism,
wherein identifying the heart region comprises:
projecting the received imaging data into a first plane of three dimensions of the received imaging data;
applying a first threshold to the first plane of data, wherein the first threshold is selected to eliminate a first pixel associated with air;
identifying a largest first connected component from the first threshold applied data;
calculating a first center of mass of the identified largest first connected component to define a first coordinate and a second coordinate;
projecting the received imaging data into a second plane of the three dimensions, wherein the second plane is perpendicular to the first plane;
applying a second threshold to the second plane of data, wherein the second threshold is selected to eliminate a second pixel associated with air;
identifying a largest second connected component from the second threshold applied data; and
calculating a second center of mass of the identified largest second connected component to define a third coordinate;
wherein a center of a heart region is defined from the defined first coordinate, the defined second coordinate, and the defined third coordinate; and
further wherein the heart region has a width in each of the three dimensions.

* * * * *